(12) United States Patent
Bliss et al.

(10) Patent No.: US 12,274,527 B2
(45) Date of Patent: Apr. 15, 2025

(54) RADAR CARDIOGRAPHY: A PRECISE CARDIAC DATA RECONSTRUCTION METHOD

(71) Applicant: Arizona Board of Regents on behalf of Arizona State University, Scottsdale, AZ (US)

(72) Inventors: Daniel W. Bliss, Scottsdale, AZ (US); Yu Rong, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 582 days.

(21) Appl. No.: 17/435,580

(22) PCT Filed: Mar. 19, 2020

(86) PCT No.: PCT/US2020/023533
§ 371 (c)(1),
(2) Date: Sep. 1, 2021

(87) PCT Pub. No.: WO2020/191142
PCT Pub. Date: Sep. 24, 2020

(65) Prior Publication Data
US 2022/0142478 A1    May 12, 2022

Related U.S. Application Data

(60) Provisional application No. 62/821,119, filed on Mar. 20, 2019.

(51) Int. Cl.
*A61B 5/00* (2006.01)
*A61B 5/024* (2006.01)
(Continued)

(52) U.S. Cl.
CPC .......... *A61B 5/0015* (2013.01); *A61B 5/0044* (2013.01); *A61B 5/02405* (2013.01);
(Continued)

(58) Field of Classification Search
CPC . A61B 5/0015; A61B 5/0044; A61B 5/02405; A61B 5/0507; A61B 5/0816;
(Continued)

(56) References Cited

U.S. PATENT DOCUMENTS 6,736,231 B2 *   5/2004   Breed .................. B60N 2/0276
                                            342/72
6,909,397 B1 *   6/2005   Greneker III ......... G01S 13/862
                                            342/28
(Continued)

FOREIGN PATENT DOCUMENTS

CN         106264501 A    1/2017
EP         3440991 A1     2/2019
(Continued)

OTHER PUBLICATIONS

Advisory Action, Examiner-Initiated Interview Summary, and AFCP 2.0 Decision for U.S. Appl. No. 16/823,587, mailed May 4, 2023, 5 pages.
(Continued)

*Primary Examiner* — Peter M Bythrow
(74) *Attorney, Agent, or Firm* — Withrow & Terranova, PLLC

(57) ABSTRACT

A precise cardiac data reconstruction method is provided, which may also be referred to herein as radar cardiography (RCG). RCG can reconstruct cardiac data, such as heart rate and/or electrocardiogram (ECG)-like heartbeat waveform signals wirelessly by using advanced radar signal processing techniques. For example, heartbeat and related characteristics can be monitored by isolating cardiovascular activity
(Continued)

from strong respiratory interference in spatial spaces: azimuth and elevation. This results in significant improvements to pulse signal-to-noise-ratio (SNR) compared to conventional approaches, facilitating heart-rate variability (HRV) analysis.

5 Claims, 18 Drawing Sheets

(51) Int. Cl.
| | |
|---|---|
| A61B 5/0507 | (2021.01) |
| A61B 5/08 | (2006.01) |
| A61B 5/11 | (2006.01) |
| A61B 5/113 | (2006.01) |
| A61B 5/16 | (2006.01) |
| G01S 7/41 | (2006.01) |
| G01S 13/02 | (2006.01) |
| G01S 13/18 | (2006.01) |
| G01S 13/89 | (2006.01) |

(52) U.S. Cl.
CPC .......... *A61B 5/0507* (2013.01); *A61B 5/0816* (2013.01); *A61B 5/1128* (2013.01); *A61B 5/1135* (2013.01); *A61B 5/16* (2013.01); *A61B 5/7207* (2013.01); *A61B 5/7257* (2013.01); *G01S 7/415* (2013.01); *G01S 13/0209* (2013.01); *G01S 13/18* (2013.01); *G01S 13/89* (2013.01)

(58) Field of Classification Search
CPC ....... A61B 5/1128; A61B 5/1135; A61B 5/16; A61B 5/7207; A61B 5/7257; G01S 7/414; G01S 7/415; G01S 13/0209; G01S 13/18; G01S 13/88; G01S 13/89
See application file for complete search history.

(56) References Cited

U.S. PATENT DOCUMENTS

| | | | | |
|---|---|---|---|---|
| 8,454,528 | B2* | 6/2013 | Yuen | A61B 5/113 600/407 |
| 8,483,761 | B2 | 7/2013 | Li et al. | |
| 9,164,167 | B2* | 10/2015 | Hyde | G01S 13/867 |
| 9,200,945 | B2* | 12/2015 | Lin | G01H 9/00 |
| 9,737,219 | B2 | 8/2017 | Chen | |
| 9,971,027 | B1* | 5/2018 | Stockmann | G01S 13/5244 |
| 10,201,278 | B2* | 2/2019 | Lux | A61B 5/024 |
| 10,753,727 | B2 | 8/2020 | Klose et al. | |
| 10,918,287 | B2 | 2/2021 | Islam | |
| 10,928,374 | B2 | 2/2021 | Islam | |
| 11,051,702 | B2* | 7/2021 | Lin | G16H 50/30 |
| 11,771,380 | B2* | 10/2023 | Rong | G06T 7/0012 |
| 2005/0128123 | A1* | 6/2005 | Greneker, III | G01S 13/888 342/28 |
| 2008/0077015 | A1* | 3/2008 | Boric-Lubecke | G01S 13/888 600/453 |
| 2008/0214903 | A1 | 9/2008 | Orbach | |
| 2010/0130873 | A1* | 5/2010 | Yuen | A61B 5/113 600/595 |
| 2010/0152600 | A1* | 6/2010 | Droitcour | A61B 5/7221 600/534 |
| 2012/0022348 | A1* | 1/2012 | Droitcour | A61B 5/0816 600/407 |
| 2012/0232388 | A1 | 9/2012 | Curra et al. | |
| 2013/0030257 | A1 | 1/2013 | Nakata et al. | |
| 2013/0300573 | A1* | 11/2013 | Brown | A61B 5/1113 340/870.01 |
| 2013/0317377 | A1 | 11/2013 | Gupta et al. | |
| 2014/0024917 | A1* | 1/2014 | McMahon | G01S 13/18 600/407 |
| 2014/0128748 | A1* | 5/2014 | Horng | G08B 13/2491 600/484 |
| 2014/0276089 | A1 | 9/2014 | Kirenko et al. | |
| 2014/0276099 | A1* | 9/2014 | Kirenko | A61B 5/0077 600/476 |
| 2014/0276104 | A1* | 9/2014 | Tao | A61B 5/7239 600/476 |
| 2014/0378809 | A1* | 12/2014 | Weitnauer | A61B 5/24 600/407 |
| 2015/0223733 | A1* | 8/2015 | Al-Alusi | A61B 5/1118 600/407 |
| 2015/0241555 | A1* | 8/2015 | Lin | A61B 5/0205 702/56 |
| 2015/0342535 | A1 | 12/2015 | Chen | |
| 2015/0379370 | A1 | 12/2015 | Clifton et al. | |
| 2016/0188831 | A1 | 6/2016 | Kurtz et al. | |
| 2016/0287208 | A1 | 10/2016 | Zhai | |
| 2016/0338604 | A1 | 11/2016 | Wang et al. | |
| 2016/0343135 | A1 | 11/2016 | De Haan et al. | |
| 2017/0042432 | A1* | 2/2017 | Adib | G01S 13/536 |
| 2017/0127988 | A1 | 5/2017 | Tao et al. | |
| 2017/0174343 | A1* | 6/2017 | Erickson | A61B 5/02055 |
| 2017/0341745 | A1* | 11/2017 | Sekine | A61N 1/3904 |
| 2018/0049669 | A1 | 2/2018 | Vu et al. | |
| 2018/0085009 | A1 | 3/2018 | Aiello et al. | |
| 2018/0085013 | A1* | 3/2018 | Cho | A61B 5/7207 |
| 2018/0140255 | A1 | 5/2018 | Tao et al. | |
| 2018/0263502 | A1* | 9/2018 | Lin | G01S 7/415 |
| 2018/0289305 | A1* | 10/2018 | Rahman | G01S 13/50 |
| 2019/0050985 | A1 | 2/2019 | Den Brinker et al. | |
| 2019/0057502 | A1 | 2/2019 | Wang et al. | |
| 2019/0077007 | A1* | 3/2019 | Mallinson | A61B 5/1128 |
| 2019/0142289 | A1* | 5/2019 | Bliss | G01S 13/582 600/407 |
| 2019/0212436 | A1 | 7/2019 | Baheti et al. | |
| 2019/0240535 | A1* | 8/2019 | Santra | A61B 5/05 |
| 2020/0037890 | A1* | 2/2020 | Cho | A61B 5/02444 |
| 2020/0196866 | A1* | 6/2020 | Chiou | G01S 13/536 |
| 2020/0271749 | A1 | 8/2020 | Wu et al. | |
| 2020/0297227 | A1 | 9/2020 | Rong et al. | |
| 2020/0302609 | A1 | 9/2020 | Rong et al. | |

FOREIGN PATENT DOCUMENTS

| | | |
|---|---|---|
| EP | 3440996 A1 | 2/2019 |
| WO | 2009009690 A2 | 1/2009 |
| WO | 2013027027 A2 | 2/2013 |
| WO | 2016185004 A1 | 11/2016 |
| WO | 2017180985 A1 | 10/2017 |
| WO | 2017195196 A1 | 11/2017 |
| WO | 2019126476 A1 | 6/2019 |
| WO | 2020072297 A1 | 4/2020 |
| WO | 2020191142 A1 | 9/2020 |
| WO | 2021202677 A1 | 10/2021 |

OTHER PUBLICATIONS

Notice of Allowance for U.S. Appl. No. 16/823,587, mailed May 26, 2023, 10 pages.

Notice of Allowance and Examiner-Initiated Interview Summary for U.S. Appl. No. 16/823,599, mailed May 31, 2023, 10 pages.

Ahmad, A. et al., "Vital signs monitoring of multiple people using a FMCW millimeter-wave sensor," 2018 IEEE Radar Conference (RadarConf18), Apr. 23-27, 2018, Oklahoma City, OK, USA, IEEE, 6 pages.

Alizadeh, M. et al., "Remote Monitoring of Human Vital Signs Using mm-Wave FMCW Radar," IEEE Access, vol. 7, Apr. 2019, IEEE, 12 pages.

Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.

Anderson, R. et al., "The Optics of Human Skin," Journal of Investigative Dermatology, vol. 77, Issue 1, Jul. 1981, Elsevier, pp. 13-19.

(56) References Cited

OTHER PUBLICATIONS

Allen, J., "Photoplethysmography and its application in clinical physiological measurement," Physiological Measurement, vol. 28, No. 3, Feb. 2007, IOP Publishing, 40 pages.
Biswas, D. et al., "Heart Rate Estimation From Wrist-Worn Photoplethysmography: A Review," IEEE Sensors Journal, vol. 19, Issue 16, Aug. 2019, IEEE, pp. 6560-6570.
Chen, K.-M. et al., "An X-Band Microwave Life-Detection System," IEEE Transactions on Biomedical Engineering, vol. BME-33, Issue 7, Jul. 1986, IEEE, 5 pages.
Chen, V.C. et al., "Micro-Doppler effect in radar: phenomenon, model, and simulation study," IEEE Transactions on Aerospace and Electronic Systems, vol. 42, Issue 1, Jan. 2006, IEEE, 20 pages.
Chen, K-M. et al., "Microwave life-detection systems for searching human subjects under earthquake rubble or behind barrier," IEEE Transactions on Biomedical Engineering, vol. 47, Issue 1, Jan. 2000, IEEE, pp. 105-114.
Chen, V. et al., "Time-Frequency Transforms for Radar Imaging and Signal Analysis," Artech House, 2002, 233 pages.
Churkin, S. et al., "Millimeter-wave radar for vital signs monitoring," 2015 IEEE International Conference on Microwaves, Communications, Antennas and Electronic Systems (COMCAS), Nov. 2-4, 2015, Tel Aviv, Israel, IEEE, 4 pages.
Damianou, D., "The wavelength dependence of the photoplethysmogram and its implication to pulse oximetry," Ph.D. Thesis, University of Nottingham, 1995, 223 pages.
Davila, M. et al., "The PhysioCam: Cardiac Pulse, Continuously Monitored by a Color Video Camera," Journal of Medical Devices, vol. 10, Issue 2, Jun. 2016, published online May 2016, 2 pages.
Fallow, B.A. et al., "Influence of skin type and wavelength on light wave reflectance," Journal of Clinical Monitoring and Computing, vol. 27, No. 3, Feb. 2013, 7 pages.
Feldman, Y. et al., "The electromagnetic response of human skin in the millimetre and submillimetre wave range," Physics in Medicine and Biology, vol. 54(11), Jul. 2009, 25 pages.
Fitzpatrick, T., "The validity and practicality of sun-reactive skin types I through VI," Archives of Dermatology, vol. 124, No. 6, Jun. 1988, pp. 869-871.
Gu, C. et al., "A Hybrid Radar-Camera Sensing System With Phase Compensation for Random Body Movement Cancellation in Doppler Vital Sign Detection," IEEE Transactions on Microwave Theory and Techniques, vol. 61, Issue 12, Dec. 2013, first published Nov. 2013, IEEE, 12 pages.
Hayut, I. et al., "The Helical Structure of Sweat Ducts: Their Influence on the Electromagnetic Reflection Spectrum of the Skin," IEEE Transactions on Terahertz Science and Technology, vol. 3, Issue 2, Mar. 2013, first published Dec. 2012, IEEE, 10 pages.
Holmes, G. et al., "Generating Rule Sets from Model Trees," 12th Australian Joint Conference on Artificial Intelligence, Dec. 1999, 9 pages.
Humphreys, K. et al., "Noncontact simultaneous dual wavelength photoplethysmography: a further step toward noncontact pulse oximetry," Review of Scientific Instruments, vol. 78, Issue 4, Apr. 2007, AIP Publishing, 7 pages.
Immoreev, I. et al., "UWB Radar for Patient Monitoring," IEEE Aerospace and Electronic Systems Magazine, vol. 23, Issue 11, Nov. 2008, IEEE, 8 pages.
It'is Foundation, "Overview—Database of Tissue Properties," 2010-2022, accessed Aug. 31, 2014 from https://itis.swiss/virtual-population/tissue-properties/database/database-summary/, 2 page.
Kamal, A. et al., "Skin photoplethysmography—a review," Computer Methods and Programs in Biomedicine, vol. 28, No. 4, Apr. 1989, pp. 257-269.
Kamshilin, A. et al., A new look at the essence of the imaging photoplethysmography, Scientific Reports, vol. 5:10494, , May 2015, 9 pages.
Kebe, M. et al., "Human Vital Signs Detection Methods and Potential Using Radars: A Review," Sensors, vol. 20, Mar. 2020, MDPI, 38 pages.
Klemm, M. et al., "Breast Cancer Detection using Symmetrical Antenna Array," The Second European Conference on Antennas and Propagation, EuCAP 2007, Nov. 11-16, 2007, Edinburgh, IET, 5 pages.
Aman, N. et al., "High-Resolution Waveguide THz Spectroscopy of Biological Molecules," Biophysical Journal, vol. 94, Issue 3, Feb. 2008, pp. 1010-1020.
Azaro, A. et al., "Analysis of Vital Signs Monitoring Using an IR-UWB Radar," Progress In Electromagnetics Research, vol. 100, Jan. 2010, pp. 265-284.
Li, C. et al., "Experiment and Spectral Analysis of a Low-Power Ka-Band Heartbeat Detector Measuring From Four Sides of a Human Body," IEEE Transactions on Microwave Theory and Techniques, vol. 54, Issue 12, Dec. 2006, IEEE, 9 pages.
Li, C. et al., "Random Body Movement Cancellation in Doppler Radar Vital Sign Detection," IEEE Transactions on Microwave Theory and Techniques, vol. 56, Issue 12, Dec. 2008, first published Nov. 18, 2008, IEEE, 4 pages.
Noon, D.A., "Stepped-Frequency Radar Design and Signal Processing Enhances Ground Penetrating Radar Performance," A thesis submitted for the degree of Doctor of Philosophy (PhD) of The University of Queensland, Jan. 1996, 186 pages.
Nowara, E. et al., "SparsePPG: Towards Driver Monitoring Using Camera-Based Vital Signs Estimation in Near-Infrared," 2018 IEEE/CVF Conference on Computer Vision and Pattern Recognition Workshops (CVPRW), Jun. 18-22, 2018, Salt Lake City, UT, USA, IEEE, 10 pages.
Orfanidis, S. J, "Electromagnetic Waves and Antennas," 2002, Rutgers University, 547 pages.
Petkie, D. et al., "Remote respiration and heart rate monitoring with millimeter-wave/terahertz radars," Proceedings of SPIE, vol. 7117, Oct. 2008, 6 pages.
Petkie, D. et al., "Millimeter-Wave Radar for Vital Signs Sensing," Radar Sensor Technology XIII Conference, Apr. 13-15, 2009, Orlando, FL, 5 pages.
Poh, M.-Z. et al., "Advancements in Noncontact, Multiparameter Physiological Measurements Using a Webcam," IEEE Transactions on Biomedical Engineering, vol. 58, Issue 1, Jan. 2011, Oct. 14, 2010, IEEE, 5 pages.
Quinlan, R., "Learning with Continuous Classes," 5th Australian Joint Conference on Artifical Intelligence, Nov. 1992, 6 pages.
Reid, C. et al., "Terahertz Time-Domain Spectroscopy of Human Blood," IEEE Journal of Biomedical and Health Informatics, vol. 17, Issue 4, Jul. 2013, first published Apr. 2013, IEEE, 11 pages.
Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.
Rong, Y. et al., "Active Breathing Suppression for Improved Sleep Monitoring Heartbeat Detection Using UWB Radar," 2019 IEEE 8th International Workshop on Computational Advances in Multi-Sensor Adaptive Processing (CAMSAP), Dec. 15-18, 2019, IEEE, 5 pages.
Rong, Y. et al., "Cardiac Sensing Exploiting an Ultra-Wideband Terahertz Sensing System," 2020 IEEE International Radar Conference (RADAR), Apr. 28-30, 2020, Washington, DC, USA, IEEE, 5 pages.
Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.
Rong, Y. et al., "Is Radar Cardiography (RCG) Possible?," 2019 IEEE Radar Conference (RadarConf), Apr. 22-26, 2019, Boston, MA, USA, IEEE, 6 pages.
Rong, Y. et al., "Multiple source detection performance of linear sparse arrays," 2016 50th Asilomar Conference on Signals, Systems and Computers, Nov. 6-9, 2016, Pacific Grove, CA, USA, IEEE, 5 pages.
Rong, Y. et al., "Non-Contact Vital Signs Detection with UAV-Borne Radars," arXiv:2011.13982v1 [eess.SP], Nov. 27, 2020, 7 pages.

(56) References Cited

OTHER PUBLICATIONS

Rong, Y. et al., "Smart Homes: See Multiple Heartbeats Through Wall Using Wireless Signals," 2019 IEEE Radar Conference (RadarConf), Apr. 22-26, 2019, Boston, MA, USA, IEEE, 6 pages.

Spetlik, R. et al., "Non-Contact Reflectance Photoplethysmography: Progress, Limitations, and Myths," 2018 13th IEEE International Conference on Automatic Face & Gesture Recognition (FG 2018), May 15-19, 2018, IEEE, 8 pages.

Staderini, E.M., "UWB Radars in Medicine," IEEE Aerospace and Electronic Systems Magazine, vol. 17, No. 1, Feb. 2002, pp. 13-18.

Sun, Y. et al., "Noncontact imaging photoplethysmography to effectively access pulse rate variability," Journal of Biomedical Optics, vol. 18, No. 6, Jun. 2013, 10 pages.

Tang, M.-C. et al., "A Self- and Mutually Injection-Locked Radar System for Monitoring Vital Signs in Real Time With Random Body Movement Cancellation," IEEE Transactions on Microwave Theory and Techniques, vol. 64, Issue 12, Dec. 2016, first published Nov. 2016, IEEE, 11 pages.

Aoyagi, T. et al., "Pulse oximetry: Its invention, contribution to medicine, and future tasks," Anesthesia and Analgesia, vol. 94, Feb. 2002, 5 pages.

Benton, C. et al., "Terahertz Radar for Remote Measurement of Vital Signs," 2008 Joint Meeting of the APS Ohio-Region Section, the AAPT Southern Ohio Section, and the ACS Dayton-Section, Oct. 10-11, 2008, Dayton, Ohio, American Physical Society, Abstract only, 1 page.

Rong, Y. et al., "Respiration and Cardiac Activity Sensing Using 3-D Cameras," 2020 54th Asilomar Conference on Signals, Systems, and Computers, Nov. 1-4, 2020, Pacific Grove, CA, USA, IEEE, 5 pages.

Theofanopoulos, P.C. et al., "A Novel Fingerprint Scanning Method Using Terahertz Imaging," 2018 IEEE International Symposium on Antennas and Propagation & USNC/URSI National Radio Science Meeting, Jul. 8-13, 2018, Boston, MA, USA, IEEE, 2 pages.

Jensen, J. et al., "Camera-based Heart Rate Monitoring," B.Sc. Thesis, Bachelor of Science in Engineering, Department of Applied Mathematics and Computer Science, Technical University of Denmark, 2014, 72 pages.

Unakafov, A., "Pulse rate estimation usinG imaging photoplethysmography: generic framework and comparison of methods on a publicly available dataset," arXiv:1710.08369v1 [eess.IV], Oct. 17, 2017, 17 pages.

Non-Final Office Action for U.S. Appl. No. 16/823,587, mailed Oct. 24, 2022, 26 pages.

Extended European Search Report for European Patent Application No. 20772680.3, mailed Nov. 8, 2022, 8 pages.

Non-Final Office Action for U.S. Appl. No. 17/277,596, mailed Aug. 18, 2023, 10 pages.

Advisory Action for U.S. Appl. No. 17/277,596, mailed Mar. 15, 2024, 3 pages.

Al-Naji, A. et al., "Remote Optical Cardiopulmonary Signal Extraction With Noise Artifact Removal, Multiple Subject Detection & Long-Distance," IEEE Access, vol. 6, 2018, IEEE, pp. 11573-11595.

Author Uknown, "Apple Watch Series 5," accessed Nov. 16, 2018 from https://www.apple.com/apple-watch-series-4/health/, 13 pages.

Author Uknown, "Shimmer3 ECG Unit," accessed Nov. 16, 2018 from http://www.shimmersensing.com/products/shimmer3-ecg-sensor, 6 pages.

Doerry, A., "Just Where Exactly is the Radar? (a.k.a. The Radar Antenna Phase Center)," Sandia Report SAND2013-10635, Dec. 2013, Sandia National Laboratories, 26 pages.

Fox, K. et al., "Resting Heart Rate in Cardiovascular Disease," Journal of the American College of Cardiology, vol. 50, No. 9, 2007, Elsevier Inc., pp. 823-830.

Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.

Li, Changzhi, "Doppler Phase Modulation Effect for Non-contact Accurate Measurement of Vital Signs and other Periodic Movements—From Theory to CMOS System on Chip Integrations," A Dissertation presented to the Graduate School of the University of Florida, 2009, 129 pages.

Lin, J., "Noninvasive Microwave Measurement of Respiration," Proceedings of the IEEE, Oct. 1975, IEEE, p. 1530.

Rong, Y. et al., "Direct RF Signal Processing For Heart-Rate Monitoring Using UWB Impulse Radar," 2018 52nd Asilomar Conference on Signals, Systems, and Computers, Oct. 28-31, 2018, Pacific Grove, CA, IEEE, pp. 1215-1219.

Rong, Y. et al., "Remote Sensing for Vital Information Based on Spectral-Domain Harmonic Signatures," IEEE Transactions on Aerospace and Electronic Systems, vol. 55, No. 6, Dec. 2019, OAPA, pp. 3454-3465.

Singh, A. et al., "Data-Based Quadrature Imbalance Compensation for a CW Doppler Radar System," IEEE Transactions on Microwave Theory and Techniques, vol. 61, No. 4, Apr. 2013, IEEE, pp. 1718-1724.

Wang, S. et al., "A Novel Ultra-Wideband 80 GHz FMCW Radar System for Contactless Monitoring of Vital Signs," 2015 37th Annual International Conference of the IEEE Engineering in Medicine and Biology Society (EMBC), Aug. 25-29, 2015, Milan, Italy, IEEE, pp. 4978-4981.

Wolff, C., "Organ-Pipe Scanner," accessed Feb. 2019 from https://www.radartutorial.eu/06.antennas/an66.en.html, 1 page.

International Search Report and Written Opinion for International Patent Application No. PCT/US2020/023533, mailed Jun. 18, 2020, 11 pages.

Fathy, Ramzie, et al., "Comparison of UWB Doppler radar and Camera based Photoplethysmography in Non-contact Multiple Heartbeats Detection," BioWireleSS, 2016, IEEE, pp. 25-28.

Feng, Litong, et al., "Motion-Resistant Remote Imaging Photoplethysmography Based on the Optical Properties of Skin," IEEE Transactions on Circuits and Systems for Video Technology, vol. 25, Issue 5, May 2015, pp. 879-891.

Gauri, Zade, "A Modern Microwave Life Detection System for Human Being Buried Under Rubble," International Journal of Advanced Engineering Research and Studies, vol. 1, Issue 1, Oct. 2011, 9 pages.

Hussain, Malek, "Ultra-Wideband Impulse Radar—An Overview of thePrinciples," IEEE AES Systems Magazine, vol. 13, Issue 9, Sep. 1998, pp. 9-14.

Lazaro, A., et al., "Analysis of Vital Signs Monitoring Using an IR-UWB Radar," Progress In Electromagnetics Research, vol. 100, 2010, pp. 265-284.

Li, Changzhi, et al., "Complex Signal Demodulation and Random Body Movement Cancellation Techniques for Non-contact Vital Sign Detection," Microwave Symposium Digest, 2008, IEEE, pp. 567-570.

Park, Byung-Kown, et al., "Arctangent Demodulation With DC Offset Compensation in Quadrature Doppler Radar Receiver Systems," IEEE Transactions on Microwave Theory and Techniques, vol. 55, Issue 5, May 2007, pp. 1073-1079.

Poh, Ming-Zher, et al., "Non-contact, automated cardiac pulse measurements using video imaging and blind source separation," Optics Express, vol. 18, Issue 10, May 2010, 13 pages.

Ren, Lingyun, et al., "Noncontact Heartbeat Detection using UWB Impulse Doppler Radar," BioWireleSS, 2015, IEEE,pp. 14-16.

Rong, Yu, et al., "Harmonics-Based Multiple Heartbeart Detection at Equal Distance using UWB Impulse Radar," IEEE Radar Conference, Apr. 2018, IEEE, pp. 1101-1105.

Singh, Megha, et al., "Reconstruction of Sequential Cardiac In-Plane Displacement Patterns on the Chest Wall by Laser Speckle Interferometry," IEEE Transactions on Biomedical Engineering, vol. 38, Issue 5, May 1991, pp. 483-489.

Wang, Jingyu, et al., "Noncontact Distance and Amplitude-Independent Vibration Measurement Based on an Extended DACM Algorithm," IEEE Transactions on Instrumentation and Measurement, vol. 63, Issue 1, Jan. 2014, pp. 145-153.

Yan, Jiaming, et al., "Through-Wall Multiple Targets Vital Signs Tracking Based on VMD Algorithm," Sensors,vol. 16, Issue 8, Aug. 2016, 11 pages.

(56) References Cited

OTHER PUBLICATIONS

Zade, G. et al., "A Modern Microwave Life Detection System for Human Being Buried Under Rubble", International Journal of Advanced Engineering Research and Studies, Oct. 2011, vol. 1, 9 pages.
Esteep, J. et al., "Recovering Pulse Rate During Motion Artifact with a Multi-Imager Array for Non-Contact Imaging Photoplethysmography," 2014 IEEE International Conference on Systems, Man, and Cybernetics, Oct. 5-8, 2014, San Diego, CA, USA, 8 pages.
Nowara, E. et al., "PPGSecure: Biometric Presentation Attack Detection Using Photopletysmograms," 12th IEEE International Conference on Automatic Face & Gesture Recognition (FG 2017), May 30-Jun. 3, 2017, Washington, DC, USA, IEEE, 3 pages.
O'Brien, S., "Deepfakes are coming. Is Big Tech ready?" CNN Money, Aug. 8, 2018, 3 pages.
Rahman, H. et al., "Real Time Heart Rate Monitoring from Facial RGB Color Video using Webcam," 9th Annual Workshop of the Swedish Artificial Intelligence Society (SAIS), May 2016, 9 pages.
Wiede, C. et al., "Remote Heart Rate Determination in RGB Data," Proceedings of the 5th International Conference on Pattern Recognition Applications and Methods (ICPRAM 2016), Feb. 2016, Scitepress, pp. 240-246.
Youseph, S. et al., "Pixel and Edge Based Illuminant Color Estimation for Image Forgery Detection," Procedia Computer Science, vol. 46, Oct. 2015, Elsevier B.V., 8 pages.
Yu et al., "Heart Rate Estimation from Facial Images using Filter Bank," 2014 6th International Symposium on Communications, Control and Signal Processing (ISCCSP), May 21-23, 2014, Athens, Greece, IEEE, 4 pages.
Non-Final Office Action for U.S. Appl. No. 16/190,687, mailed Jan. 12, 2021, 14 pages.
Final Office Action for U.S. Appl. No. 16/190,687, mailed May 12, 2021, 5 pages.
Advisory Action for U.S. Appl. No. 16/190,687, mailed Jul. 26, 2021, 3 pages.
Notice of Allowance for U.S. Appl. No. 16/190,687, mailed Aug. 31, 2021, 9 pages.
Notice of Allowance for U.S. Appl. No. 16/190,687, mailed Dec. 24, 2021, 9 pages.
Non-Final Office Action for U.S. Appl. No. 16/823,587, mailed Nov. 23, 2021, 19 pages.
Final Office Action for U.S. Appl. No. 16/823,587, mailed May 25, 2022, 34 pages.
Al-Naji, A. et al., "Remote measurement of cardiopulmonary signal using an unmanned aerial vehicle," IOP Conference Series: Materials Science and Engineering, vol. 405, Sep. 2018, IOP Publishing, 10 pages.
Final Office Action and Examiner-Initiated Interview Summary for U.S. Appl. No. 16/823,587, mailed Mar. 2, 2023, 25 pages.
Non-Final Office Action for U.S. Appl. No. 16/823,599, mailed Feb. 1, 2023, 13 pages.
Final Office Action for U.S. Appl. No. 17/277,596, mailed Dec. 28, 2023, 10 pages.
Tang, M.-C. et al., "Single Self-Injection-Locked Radar With Two Antennas for Monitoring Vital Signs With Large Body Movement Cancellation," IEEE Transactions on Microwave Theory and Techniques, vol. 65, Issue 12, Dec. 2017, first published Nov. 2017, IEEE, 10 pages.
Theofanopoulos, P.C. et al., "A Terahertz Microscopy Technique for Sweat Duct Detection," 2018 IEEE/MTT-S International Microwave Symposium—IMS, Jun. 10-15, 2018, Philadelphia, PA, USA, IEEE, 4 pages.
Tripathi, S. et al., "Morphology of human sweat ducts observed by optical coherencetomography and their frequency of resonance in the terahertz frequency region," Scientific Reports, vol. 5, Article No. 9071, Mar. 2015, 7 pages.
Verkruysse, W. et al., "Remote plethysmographic imaging using ambient light," Optics Express, vol. 16, No. 26, Dec. 2008, 16 pages.
Wang, F.-K. et al., "Detection of Concealed Individuals Based on Their Vital Signs by Using a See-Through-Wall Imaging System With a Self-Injection-Locked Radar," IEEE Transactions on Microwave Theory and Techniques, vol. 61, Issue 1, Jan. 2013, Dec. 2012, IEEE, 9 pages.
Wang, W. et al., "Unsupervised Subject Detection via Remote-PPG," IEEE Transactions on Biomedical Engineering, vol. 62, No. 11, Nov. 2015, first published Jun. 2015, IEEE, 9 pages.
Wang, Y. et al., "Induction of model trees for predicting continuous classes," Proceedings of the poster papers of the 9th European Conference on Machine Learning, Apr. 1997, 12 pages.
Zhang, Q. et al., "Heart Rate Extraction Based on Near-Infrared Camera: Towards Driver State Monitoring," IEEE Access, vol. 6, Jun. 2018, IEEE, 11 pages.
Zhu et al., "Doppler Radar Techniques for Vital Signs Detection Featuring Noise Cancellations," 2019 IEEE MTT-S Interational Microwave Biomedical Conference, May 2019, IEEE, 6 pages.
Invitation to Pay Additional Fees for International Patent Application No. PCT/US2019/053425, mailed Nov. 27, 2019, 2 pages.
International Search Report and Written Opinion for International Patent Application No. PCT/US2019/053425, mailed Jan. 30, 2020, 10 pages.
International Preliminary Report on Patentability for International Patent Application No. PCT/US2019/053425, mailed Apr. 15, 2021, 7 pages.
International Search Report and Written Opinion for International Patent Application No. PCT/US2021/025106, mailed Jul. 20, 2021, 10 pages.
Notice of Allowance and Examiner-Initiated Interview Summary for U.S. Appl. No. 17/277,596, mailed Jun. 3, 2024, 10 pages.
Yang, Z. et al., "Monitoring Vital Signs Using Millimeter Wave," MobiHoc '16: Proceedings of the 17th ACM International Symposium on Mobile Ad Hoc Networking and Computing, Jul. 2016, ACM, 10 pages.

\* cited by examiner

RADAR CARDIOGRAPHY: A PRECISE
CARDIAC DATA RECONSTRUCTION
METHOD

RELATED APPLICATIONS

This application is a 35 U.S.C. § 371 national phase filing of International Application No. PCT/US20/23533, filed Mar. 19, 2020, which claims the benefit of provisional patent application Ser. No. 62/821,119, filed Mar. 20, 2019, the disclosures of which is hereby incorporated herein by reference in its entirety.

FIELD OF THE DISCLOSURE

This disclosure is related to remote vital sign detection.

BACKGROUND

Remote sensing of physiological parameters, such as heartbeat and breathing, has a number of uses. For example, this can facilitate prevention and early diagnosis of cardiovascular diseases. Two-thirds of the cost of healthcare in the US is due to chronic diseases. One of the leading chronic diseases in developed countries and one of the major causes of death in US is cardiovascular disease. There is a strong demand for providing timely heart health information in a convenient and less-expensive way for cardiologists, potential patients, or even normal people living their daily lives. Conventional medical devices, such as electrocardiograms (ECGs), and more recent smart devices, such as smart wearable devices, can provide accurate heart rate measurement but require direct contact with the human body. These existing approaches can cause discomfort and may not be suitable for long-term monitoring of physiological parameters.

SUMMARY

A precise cardiac data reconstruction method is provided, which may also be referred to herein as radar cardiography (RCG). RCG can reconstruct cardiac data, such as heart rate and/or electrocardiogram (ECG)-like heartbeat waveform signals wirelessly by using advanced radar signal processing techniques. For example, heartbeat and related characteristics can be monitored by isolating cardiovascular activity from strong respiratory interference in spatial spaces: azimuth and elevation. This results in significant improvements to pulse signal-to-noise-ratio (SNR) compared to conventional approaches, facilitating heart-rate variability (HRV) analysis.

Image processing techniques may be applied in reconstruction of the cardiac data. For example, a three-dimensional (3-D) image of a region of interest may be formed from a series of collected radar signals. The region of interest may be indicated by clustered energy indicating chest motion from cardiac and/or respiratory activity. The region of interest may be a region in space, and in some cases may further be a range of time. The 3-D image may be further processed to find respiration data and/or cardiac data. In some examples, the heart rates of multiple subjects can be monitored using ultra-wideband (UWB) impulse radar. The heart rates may further be monitored through objects, such as a wall. These examples may be robust against small-scale body motion, such as hand motion from cellphone usage or typing over a laptop.

In some examples, autonomous flying technology can be combined with RCG to implement a BioDrone system. The BioDrone system is a smart and flexible flying platform for search and rescue of humans in hostile environments. The BioDrone system can remotely measure vital signs of stationary subjects up to several meters using a UWB radar sensor. The BioDrone can be useful in life-endangering situations, such as earthquakes, fires, and floods, and can sense subjects behind objects (e.g., walls and building structures).

An exemplary aspect relates to a method for reconstructing vital signs of a subject. The method includes receiving a first radar signal measuring a region of interest of the subject and forming a first 3-D image of the region of interest. The method also includes reconstructing a respiration waveform from the first 3-D image and reconstructing cardiac data based on the first 3-D image and the respiration waveform.

Another exemplary aspect relates to a vital sign monitoring system. The vital sign monitoring system includes a radar sensor and a signal processor. The signal processor is configured to receive a radar signal from the radar sensor and form a slow-time image of a region of interest of a first human subject from the radar signal. The signal processor is further configured to remove static body parts from the slow-time image and extract a vital sign signal from the slow-time image.

Another exemplary aspect relates to a device. The device includes a radar sensor and a signal processor. The signal processor is configured to receive a first radar signal from the radar sensor and locate a potential human subject in the first radar signal. The signal processor is further configured to receive a second radar signal from the radar sensor focused to the potential human subject and extract a vital sign signal of the potential human subject using the second radar signal.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1A:
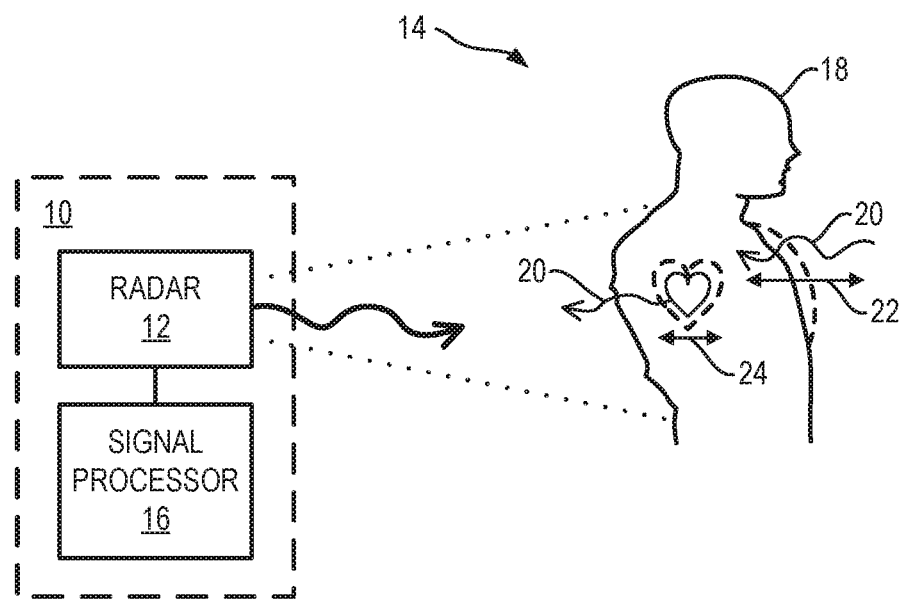
FIG. 1A is a schematic diagram of an exemplary vital sign monitoring system, which may also be referred to as a radar cardiography (RCG) system.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A precise cardiac data reconstruction method is provided, which may also be referred to herein as radar cardiography (RCG). RCG can reconstruct cardiac data, such as heart rate and/or electrocardiogram (ECG)-like heartbeat waveform signals wirelessly by using advanced radar signal processing techniques. For example, heartbeat and related characteristics can be monitored by isolating cardiovascular activity from strong respiratory interference in spatial spaces: azimuth and elevation. This results in significant improvements to pulse signal-to-noise-ratio (SNR) compared to conventional approaches, facilitating heart-rate variability (HRV) analysis.

Image processing techniques may be applied in reconstruction of the cardiac data. For example, a three-dimensional (3-D) image of a region of interest may be formed from a series of collected radar signals. The region of interest may be indicated by clustered energy indicating chest motion from cardiac and/or respiratory activity. The region of interest may be a region in space, and in some cases may further be a range of time. The 3-D image may be further processed to find respiration data and/or cardiac data. In some examples, the heart rates of multiple subjects can be monitored using ultra-wideband (UWB) impulse radar. The heart rates may further be monitored through objects, such as a wall. These examples may be robust against small-scale body motion, such as hand motion from cellphone usage or typing over a laptop.

In some examples, autonomous flying technology can be combined with RCG to implement a BioDrone system. The BioDrone system is a smart and flexible flying platform for search and rescue of humans in hostile environments. The BioDrone system can remotely measure vital signs of stationary subjects up to several meters using a UWB radar sensor. The BioDrone can be useful in life-endangering situations, such as earthquakes, fires, and floods, and can sense subjects behind objects (e.g., walls and building structures).

I. Radar Cardiography (RCG)

FIG. 1A is a schematic diagram of an exemplary vital sign monitoring system, which may also be referred to as an RCG system 10. The RCG system 10 includes a radar sensor 12 which senses a nearby environment 14 by sending and receiving wireless signals from one or more antennas. The radar sensor 12 is coupled to a signal processor 16, which is used to reconstruct a 3-D image of the environment 14 from multiple transmit-receive antenna pairs of the radar sensor 12. A radio frequency (RF) response of vital sign motion (e.g., motions related to measuring physiological parameters) of a human subject 18 is modeled as a superposition of responses from discrete, dynamic scattering centers 20, which may be from chest movement from respiratory activity 22 and cardiac activity 24. In some examples, the radar sensor 12 has multiple antennas (e.g., eighteen transmit and receive pairs), and operates on an impulse signaling scheme with a wide bandwidth and a center frequency greater than 5 gigahertz (GHz) (e.g., a 7 GHz bandwidth with a center frequency of 6.85 GHz). The radar sensor 12 may have a detection range of 3 meters (m) or greater, depending on conditions and RF parameters.

In an exemplary aspect, an i-th scattering center 20 is parameterized by reflectivity coefficient $\rho_i(t)$ and radial distance $d_i(t)$ from the radar sensor, which vary as a function of time t. The received composite signal is modeled as follows:

$$y(\tau, t) = \Sigma_i^N \rho_i(t) p(\tau - \tau_{d_i}(t)) \quad \text{Equation 1}$$

$$= \Sigma_i^N \rho_i(t) p\left(\tau - 2\frac{d_i(t)}{c}\right) \quad \text{Equation 2}$$

where N is the number of scattering centers and $p(\tau)$ is the transmitted pulse. c denotes the speed of light. Note that t and $\tau$ are two different time scales. The former is often referred to as a slow-time sampling interval and is related to the pulse repetition interval. The latter time scale is referred as a fast-time sampling interval and is often associated with an analog-to-digital converter (ADC) sampling interval providing distance information.

By analyzing a single 3-D image, a highly reflective object can be identified; by analyzing multiple consecutive 3-D images, the motion of a moving subject can be traced. With an improved number of antennas in both azimuth and elevation domains along with a high signaling bandwidth, a fine 3-D resolution cube is achieved in the space. The target of interest can therefore be possibly isolated from a noisy environment. Detailed information of the target can be extracted by further processing the radar image pixels in the region of interest. For example, minute motion of vital sign activities of human beings can be estimated.

Figure 1B:
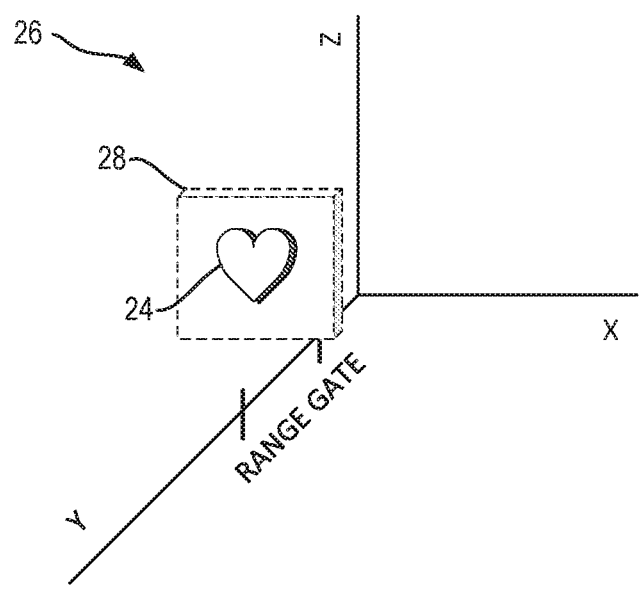
FIG. 1B is a schematic diagram of a three-dimensional (3-D) image of a region of interest of the environment of FIG. 1A, which includes cardiac activity of the subject.

FIG. 1B is a schematic diagram of a 3-D radar image 26 of a region of interest 28 of the environment 14 of FIG. 1A, which includes cardiac activity 24 of the subject 18. The region of interest 28 can be readily isolated in azimuth (e.g., x-axis), elevation (e.g., z-axis), and/or range (e.g., y-axis) after thresholding and removing background noise. The 3-D radar image 26 can provide not only location information of the region of interest 28, it also provides potential motion information if analyzing changes in multiple images (e.g., locating and analyzing the region of interest 28 in both space and time).

An exemplary method for reconstructing respiratory activity of a subject uses an embodiment of the radar sensor 12 having a field of view of approximately 60 degrees horizontally and 60 degrees vertically. In an exemplary aspect, the detection range can be set to a relatively small motion range corresponding to vital signs (e.g., between 5 centimeters (cm) and 15 cm). In the 3-D radar image 26, the peak pixel intensity corresponds to the chest motion and can be located after removing the static body parts by analyzing a sequence of 3-D images. The nearby image pixels within the energy cluster are spatially averaged to form a single sample point related to respiratory activity. These image pixel locations are recorded as the region of interest and are used for processing subsequent radar images. By performing this spatial averaging operation on consecutive radar images at a fixed region of interest, a time series approximating the chest motion is obtained.

An exemplary method for cardiac data reconstruction can separate the relatively weak heartbeat signal from the relatively strong respiration signal based on simple geometry using spatial degree-of-freedom. In a first sensing period, the significant respiratory activity occurs at a center location represented by a tuple of $(d_{Vital}, \alpha_{resp}, \beta_{resp})$ in the 3-D space, where $\alpha_{resp}$ and $\beta_{resp}$ denote the angular information in azimuth and elevation domains. In a second sensing period, the detection range is adjusted to $d_{Vital} +/- d_0$, where $d_0$ is chosen as 3 cm. The spatial location of the heart can be located as of $(\alpha_{hr}, \beta_{hr})$ based on the prior knowledge of where the heart chamber is in azimuth and elevation. In general, the respiratory energy at depth $d_{Vital}$ spreads across a much larger area in azimuth and elevation than that of the cardiac energy. Based on this fact, the heartbeat region of interest in 3-D space is selected as a small 3-D contour centered at $(d_{Vital}, \alpha_{resp}, \beta_{resp})$. The selected small contour represents scattering from motion corresponding to cardiac activity.

In some examples, the heartbeat region of interest is fixed across all images in order to obtain the maximum heartbeat sensitivity. By spatial averaging the radar pixels in the region of interest centered at $(d_{Vital}, \alpha_{hr}, \beta_{hr})$ at each scan, a time series containing the cardiovascular activity is obtained with respiration significantly suppressed. Each pixel within the heartbeat region of interest can be viewed as an independent channel containing the common pulse information but with independent channel noise. By spatial averaging these channels, the pulse SNR is enhanced. A motion filter is applied to the concatenated time series at the frequency band of interest to focus on the heartbeat motion.

Figure 2:
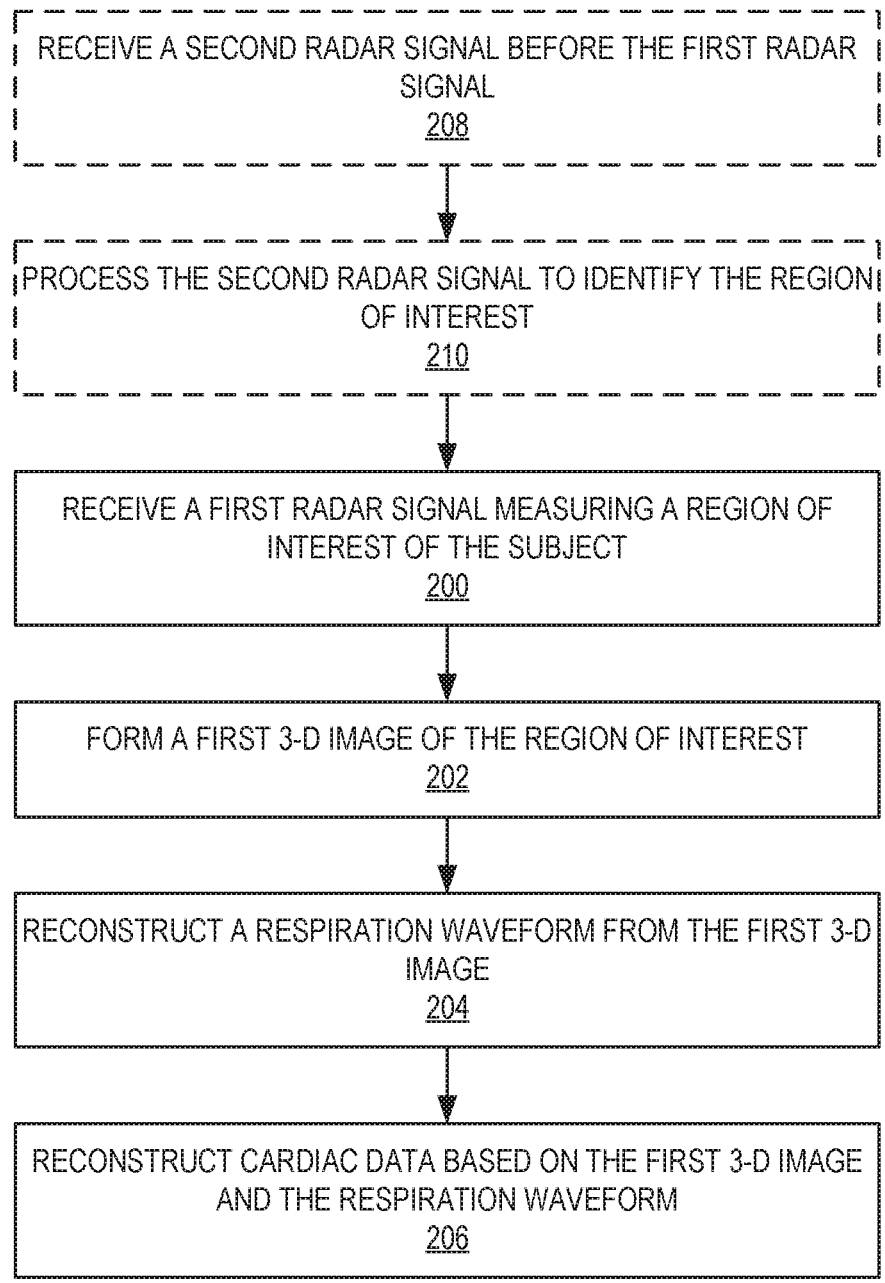
FIG. 2 is a block diagram of an exemplary method for reconstructing vital signs of a subject according to embodiments disclosed herein.

FIG. 2 is a block diagram of an exemplary method for reconstructing vital signs of a subject (e.g., the human subject 18 of FIG. 1A) according to embodiments disclosed herein. In an exemplary aspect, the method begins at step 200, with receiving a first radar signal measuring a region of interest of the subject. The method continues at step 202, with forming a first 3-D image of the region of interest. The method continues at step 204, with reconstructing a respiration waveform from the first 3-D image. The method continues at step 206, with reconstructing cardiac data based on the first 3-D image and the respiration waveform. In some examples, the method may optionally include step 208, with receiving a second radar signal before the first radar signal. The method may further include step 210, with processing the second radar signal to identify the region of interest.

Figure 3:
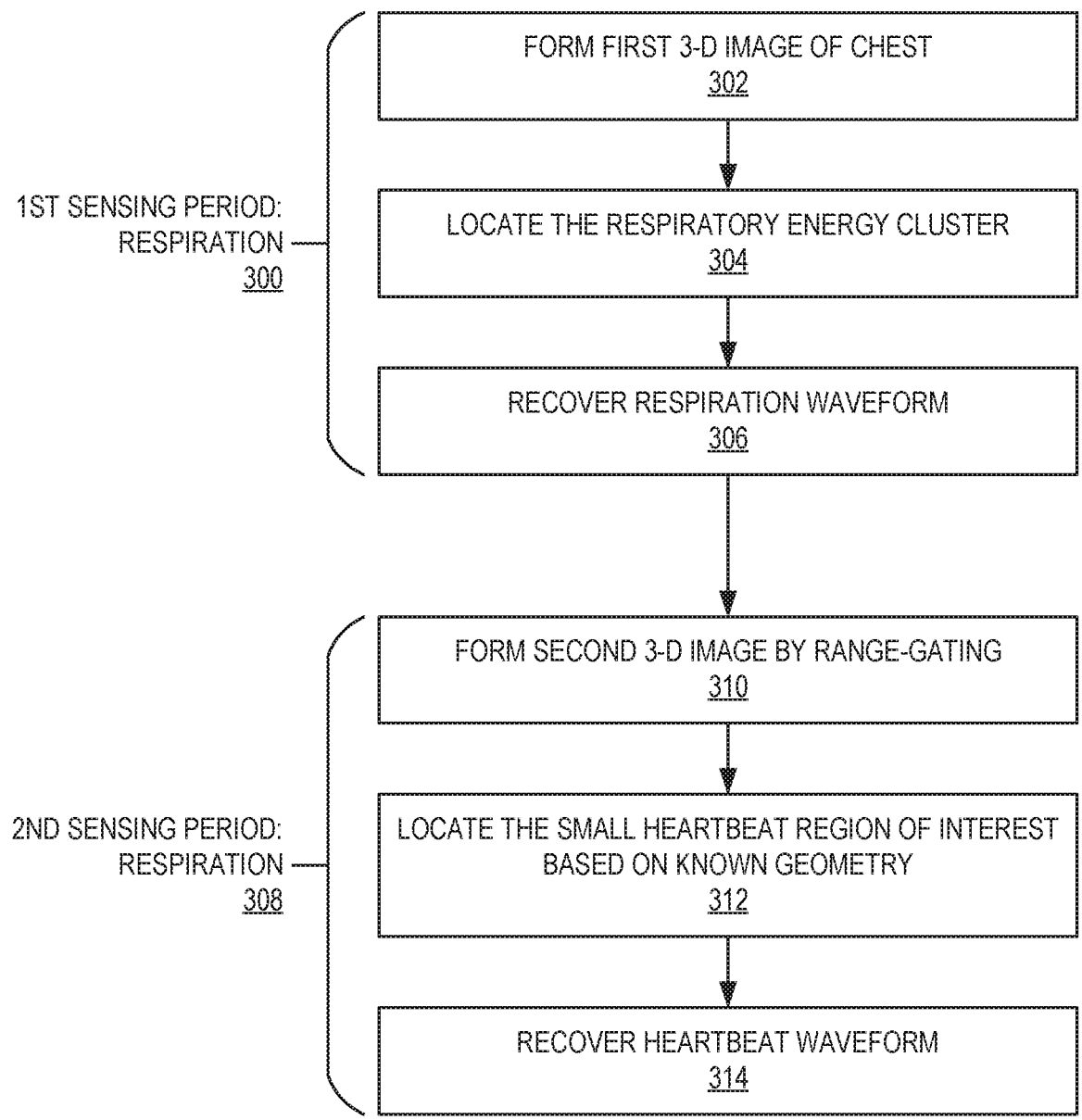
FIG. 3 is a block diagram of an exemplary heartbeat monitoring algorithm according to additional embodiments described herein.

FIG. 3 is a block diagram of an exemplary heartbeat monitoring algorithm according to additional embodiments described herein. This diagram summarizes the processing techniques described above. In a first sensing period 300, a first 3-D radar image of the human subject 18 of FIG. 1 is formed (block 302). The strongest energy cluster in the radar image corresponds to the respiratory activity after motion filtering. The center location is recorded as $(d_{Vital}, \alpha_{resp}, \beta_{resp})$ (block 304). Image pixels from the cluster are spatially averaged to obtain a single denoised respiration sample. The respiratory variation is obtained by processing multiple consecutive image frames at a common respiration region of interest (block 306).

In a second sensing period 308, the range-gate is adjusted to where most of the vital sign energy occurs and a second 3-D radar image is formed (block 310). In the updated second 3-D radar image (which is formed from the same set of radar signal data as the first 3-D radar image), a small heartbeat region of interest is selected in order to suppress the majority of the respiratory interference (block 312). Similarly, the heartbeat waveform is obtained by concatenating the individual spatially averaged image pixels (block 314).

Experimental results show results of using the system and methods for RCG using a radar sensor described above. First, the pulse SNR performance of the proposed RCG method in 3-D space is compared to that of the conventional radar signal processing technique in temporal domain and spectral domain. Significant pulse SNR improvement is demonstrated. Second, HRV analysis is conducted on the reconstructed heartbeat waveform by comparing against the reference ECG signal.

Figure 4A:
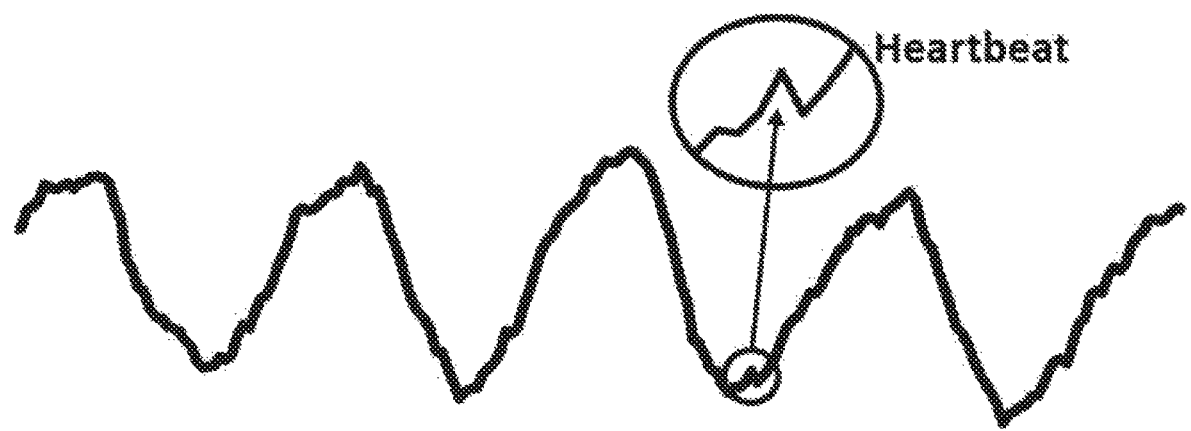
FIG. 4A is a graphical representation of a temporal waveforms from a conventional radar approach.
Figure 4B:
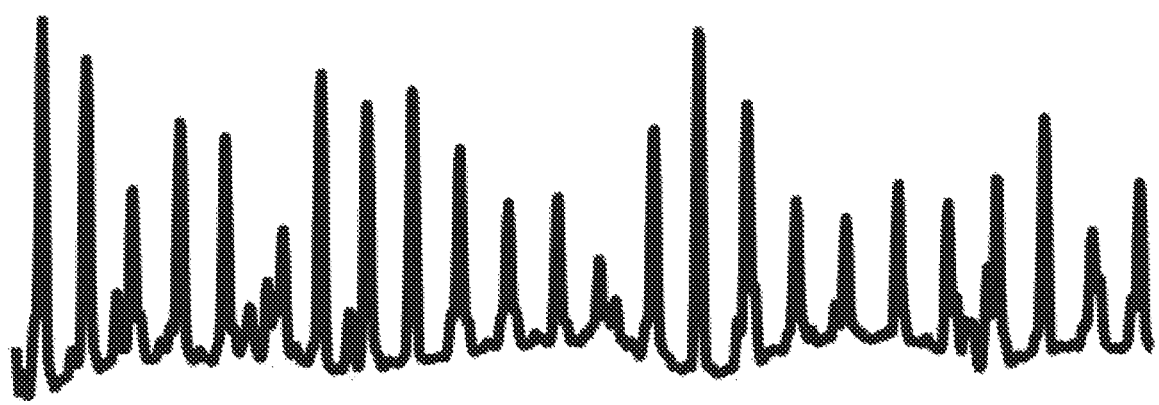
FIG. 4B is a graphical representation of a temporal waveform from the exemplary RCG system and methods of FIGS. 1A-3.

FIG. 4A is a graphical representation of a temporal waveform from a conventional radar approach. FIG. 4B is a graphical representation of a temporal waveform from the exemplary RCG system 10 and methods of FIGS. 1A-3. The conventional approach uses a radar sensor with a single transceiver placed in front of a human subject about 1 m away. In the conventional result of FIG. 4A, the overall waveform is dominated by respiration motion while tiny peaks on the top of the overall respiration pattern correspond to the heartbeat. In contrast, the reconstructed heartbeat waveform of FIG. 4B from the proposed RCG method successfully suppresses the respiration-interference and provides clean heartbeat waveform measurement.

Figure 5C:
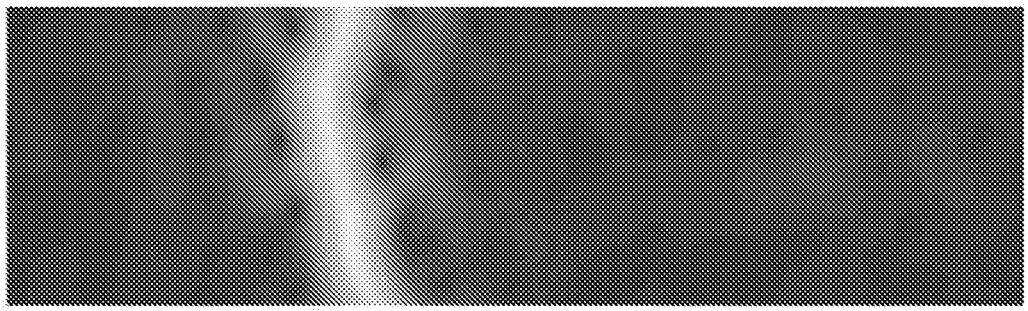
FIG. 5C is a graphical representation of a spectral waterfall plot from a reference electrocardiogram (ECG) signal.
Figure 5B:
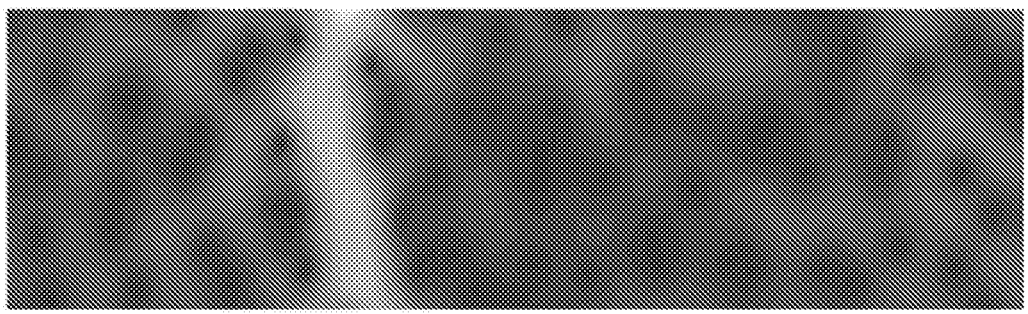
FIG. 5B is a graphical representation of a spectral waterfall plot from the exemplary RCG system of FIG. 4B.
Figure 5A:
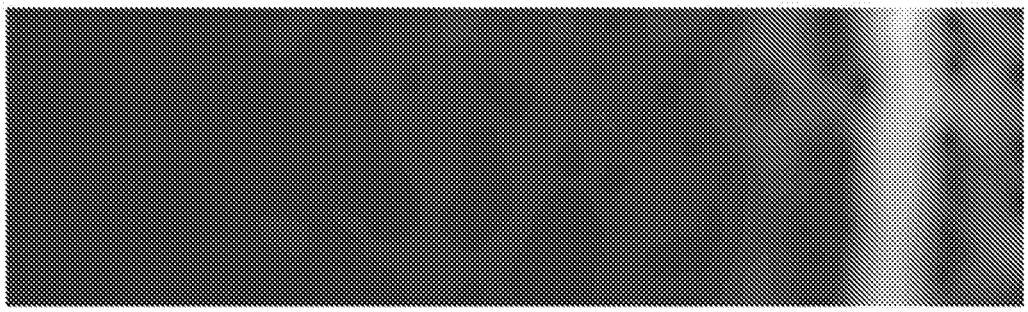
FIG. 5A is a graphical representation of a spectral waterfall plot from the conventional radar approach of FIG. 4A.

FIG. 5A is a graphical representation of a spectral waterfall plot from the conventional radar approach of FIG. 4A. FIG. 5B is a graphical representation of a spectral waterfall plot from the exemplary RCG system 10 of FIG. 4B. FIG. 5C is a graphical representation of a spectral waterfall plot from a reference ECG signal. The horizontal axis in FIGS. 5A-5C denotes time in seconds, and the vertical axis denotes frequency in beats/breaths per minute (BPM). For the conventional method of FIG. 5A, the heart-rate evolution over time is not visible due to the strong respiration-interference and low pulse SNR. The heart-rate evolution from the proposed method of FIG. 5B is distinct and consistent with result from the reference ECG signal of FIG. 5C.

Figure 6C:
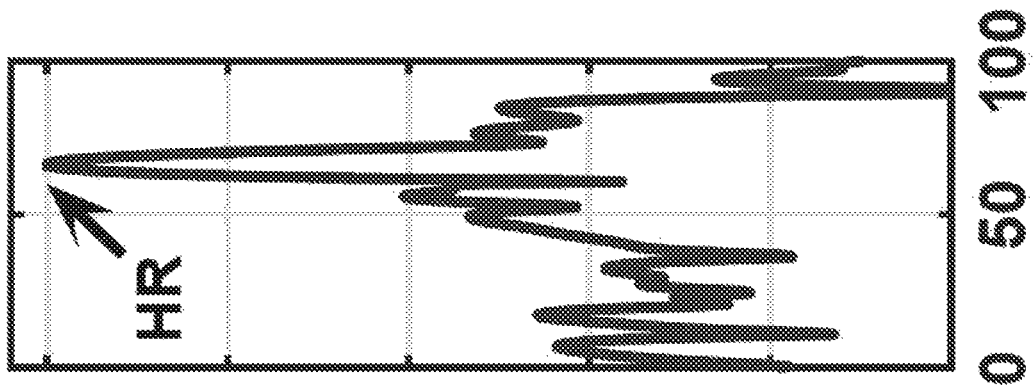
FIG. 6C is a graphical representation of one snapshot of heartbeat spectral results from the reference ECG signal of FIG. 5C.
Figure 6B:
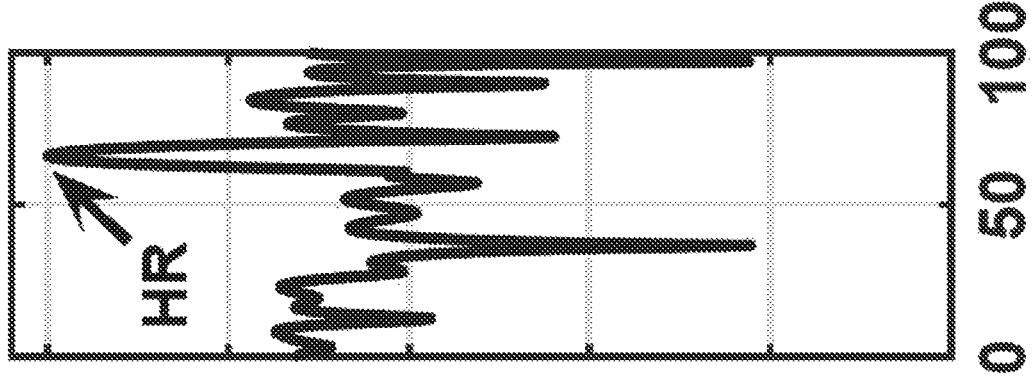
FIG. 6B is a graphical representation of one snapshot of heartbeat spectral results from the exemplary RCG system of FIG. 5B.
Figure 6A:
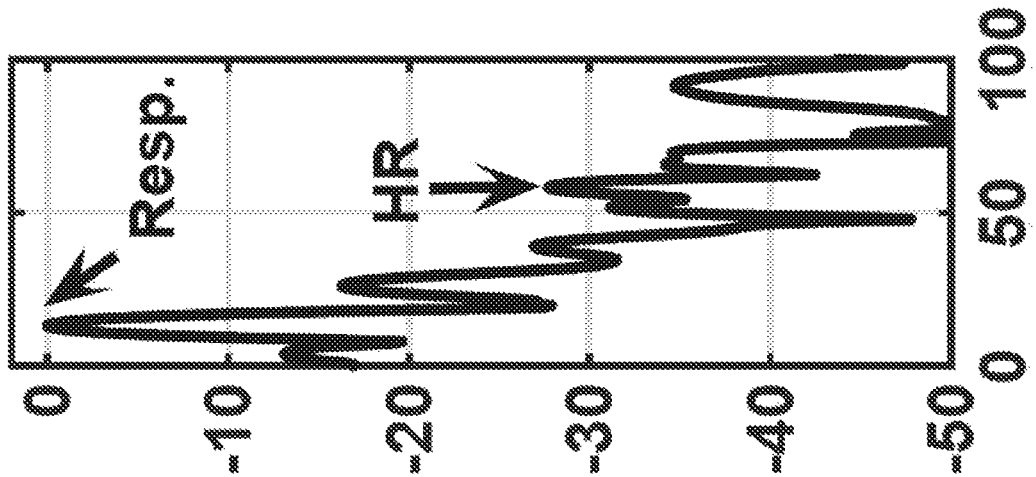
FIG. 6A is a graphical representation of one snapshot of heartbeat spectral results from the conventional radar approach of FIG. 5A.

FIG. 6A is a graphical representation of one snapshot of heartbeat spectral results from the conventional radar approach of FIG. 5A. FIG. 6B is a graphical representation of one snapshot of heartbeat spectral results from the exemplary RCG system 10 of FIG. 5B. FIG. 6C is a graphical representation of one snapshot of heartbeat spectral results from the reference ECG signal of FIG. 6C. The horizontal axis in FIGS. 6A-6C denotes frequency in BPM and the vertical axis denotes relative spectral power in decibels (dB). In the traditional radar approach, spectral analysis is often used to estimate the rate because of the strong respiration-interference and low pulse SNR in the time domain. As shown in FIG. 6A, a phase-based method with DC calibration technique is applied to generate this result. The respiration harmonics, however, are not effectively suppressed. Only with the help of an external reference can the heartbeat be identified. In contrast, the proposed RCG method of FIG. 6B generates a much cleaner spectrum with almost no respiration interference. The heartbeat spectral location is identical with that of the ECG reference of FIG. 6C.

Figure 7:
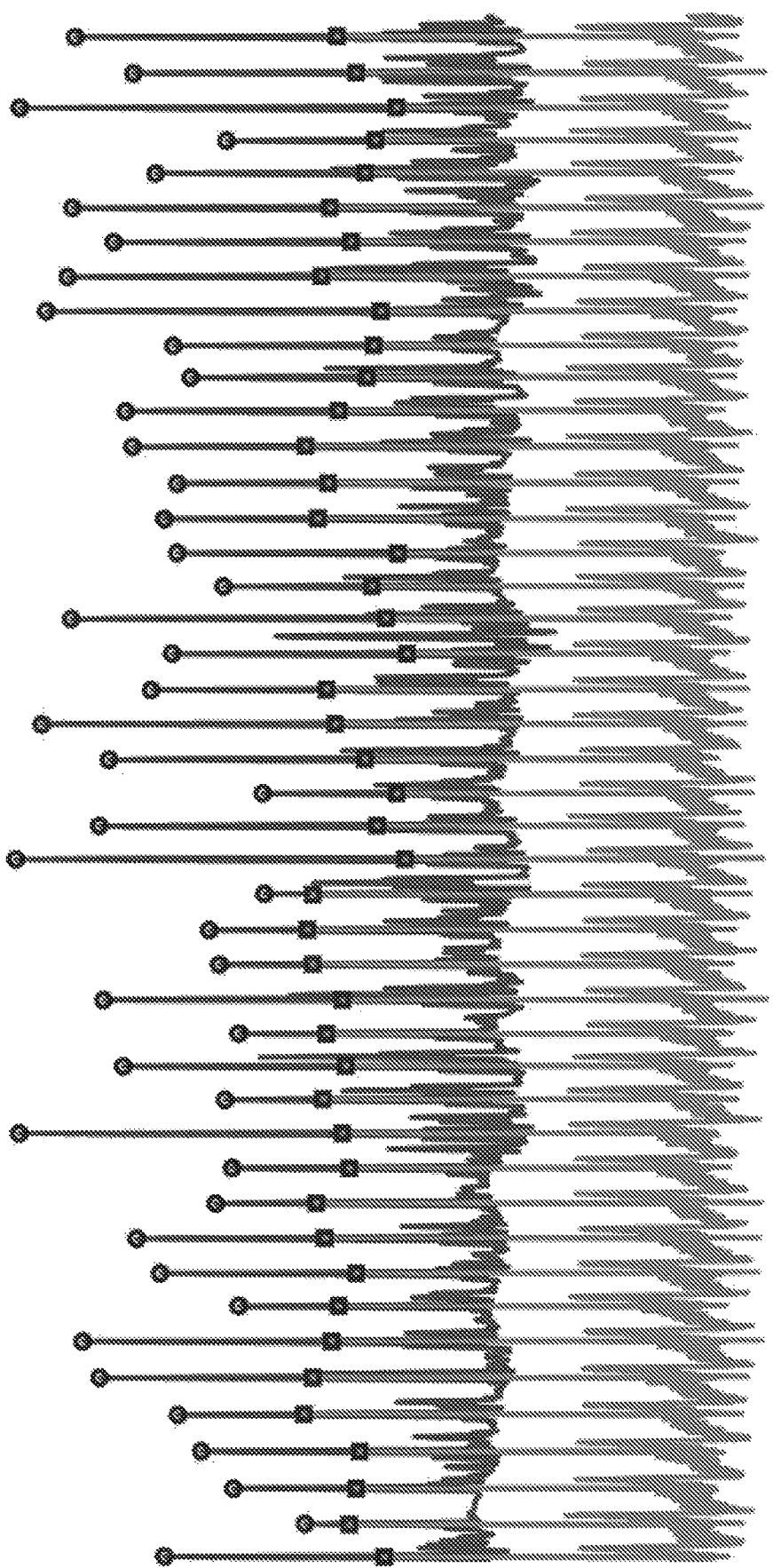
FIG. 7 is a graphical comparison of heartbeat waveforms from the exemplary RCG system with the reference ECG signal.

FIG. 7 is a graphical comparison of heartbeat waveforms from the exemplary RCG system 10 with the reference ECG signal. The top curve is a 60-second reconstructed heartbeat waveform using the proposed RCG method, while the bottom curve is a corresponding 60-second reference ECG waveform. All the R-peaks are marked in the reconstructed waveform and they are precisely aligned with the reference signal.

Figure 8A:
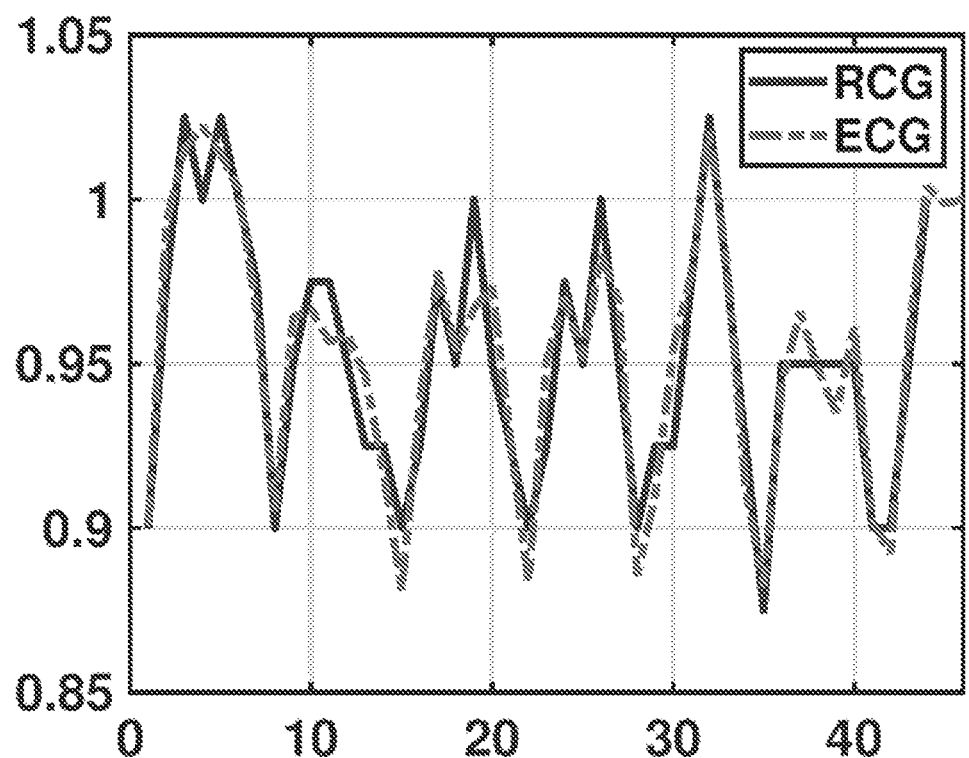
FIG. 8A is a graphical comparison of R-peak to R-peak (R-R) intervals from the exemplary RCG system and methods of FIGS. 1A-3 with the reference ECG signal.
Figure 8B:
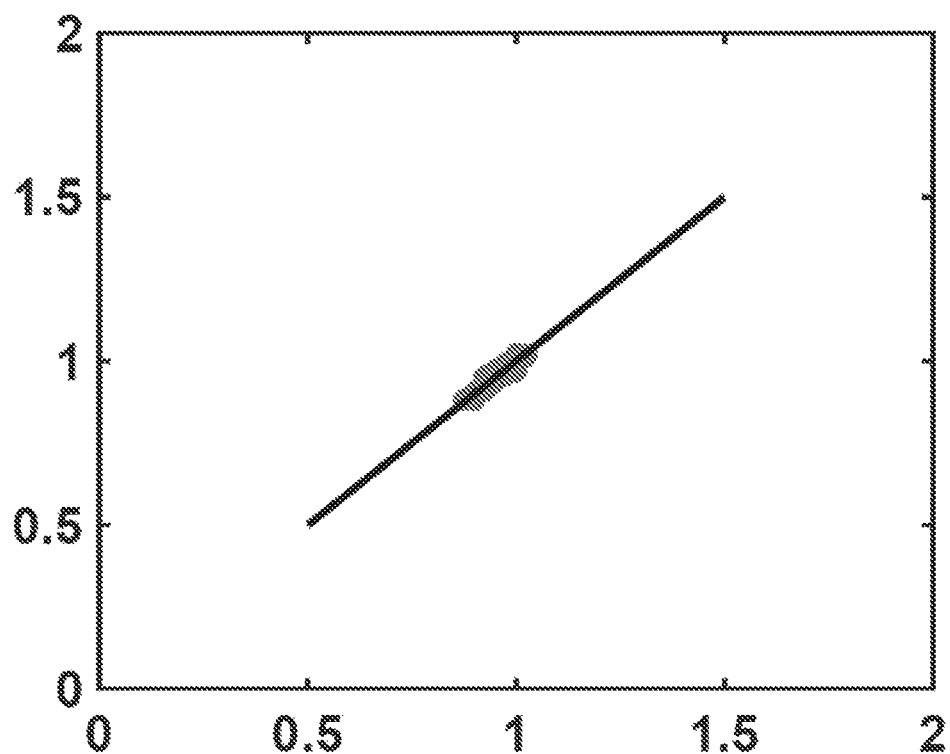
FIG. 8B is a graphical comparison of R-R intervals from the exemplary RCG system and methods of FIGS. 1A-3 with the reference ECG signal.

FIGS. 8A and 8B demonstrate the accuracy of the proposed heartbeat waveform reconstruction method by comparing the estimated R-peak to R-peak (R-R) intervals to those of the reference ECG signal. The R-R interval estimation error is on the order of 10 milliseconds (ms). FIG. 8A is a graphical comparison of R-R intervals from the exemplary RCG system 10 and methods of FIGS. 1A-3 with the reference ECG signal. The horizontal axis denotes index number and the vertical axis denotes R-R interval in seconds. FIG. 8B is a graphical comparison of R-R intervals from the exemplary RCG system 10 and methods of FIGS. 1A-3 with the reference ECG signal. The horizontal axis denotes the computed R-R interval from the RCG signal and the vertical axis denotes the R-R interval from the reference ECG signal. The black diagonal line denotes the baseline.

II. Multiple-Subject and Through-Wall Detection

Here, an exemplary model is presented for detecting physiological parameters (e.g., vital signs) using a UWB impulse radar. A vital sign signal is actually preserved RF signal domain. Down-conversion to complex-baseband is performed in digital domain. Then vital signs can be extracted using a complex signal demodulation method and phase-based methods in complex-baseband. But an undesirable phase offset might occur in the down-conversion process due to the carrier mismatch. This phase offset reduces the signal strength of the vital signs, and should be measured and compensated.

The captured radar returns are often organized in a two-dimensional (2-D) array, fast-time and slow-time. They are on very different time scales. The fast-time sampling time (which often corresponds to the range direction) is usually on the order of nanoseconds and the output slow-time sampling time is on the order of microseconds. The fast sampling time is denoted $\tau$ and the transformed frequency component is denoted v, while t denotes the slow cross-range sample time and f is the corresponding Fourier domain component. The vital signs of a subject at a nominal distance $d_0$ can be simplified as a sum of two periodic motions from respiratory and cardiac activities:

$$v(t) = d_0 + M_b \sin(2\pi f_b t) + M_h \sin(2\pi f_h t) \qquad \text{Equation 3}$$

where $M_b$ is the amplitude of respiratory activity, and $M_h$ is the amplitude of cardiac activity. $f_b$ and $f_h$ are respiration and heartbeat frequencies.

The received signal can be modeled as a product of the target response and the delayed versions of the transmitted pulse. The vital sign is related to the time-varying delay as a function of the slow-time t.

$$r(t,\tau) = A_T p(\tau - \tau_D(t)) \qquad \text{Equation 4}$$

where $p(t,\tau)$ is the generated short pulse, centered at the carrier frequency $F_c$. $A_T$ denotes the magnitude of the target response, and $$\tau_D(t) = \frac{2(d_0 + V(t))}{c} = \tau_0 + \frac{2V(t)}{c}$$

denotes the time-varying delay. c is the speed of light. The received signal is then down-converted to the complex baseband and is represented as:

$$y(t,\tau) = A_T p(\tau - \tau_D(t)) e^{-j2\pi F_c \tau} \qquad \text{Equation 5}$$

The modulation on time-delay from the chest motion can be extracted by performing Fourier analysis. Through forward and backward Fourier transforms with respect to t and $\tau$, the Fourier transform of Equation 5 with respect to t is given as:

$$|Y(f,\tau_0)| = \sum_{k=-\infty}^{\infty} \sum_{l=-\infty}^{\infty} |C_{k,l}(\tau_0)| \delta(f - kf_b - lf_h) \ge |Y(f,\tau)| \qquad \text{Equation 6}$$

where $C_{k,l}(\tau) = \int dv[P(v+F_c)e^{j2\pi v(\tau-\tau_0)}J_k(4\pi(v+F_c)M_b/c)J_l(4\pi(v+F_c)M_h/c)]$. P(v) denotes the Fourier transform of the transmitted pulse $p(\tau)$ and $J_k(.)$ denotes the Bessel function of the first kind. The absolute value of the complex coefficient $C_{k,l}(\tau)$ achieves its maximum at the delay $\tau_0$. The subscripts k and l are harmonics order of respiration and heartbeat.

In an exemplary aspect, a robust heart-rate estimation method traces the fundamental heartbeat and its associated higher-order harmonics in the spectral domain. Since the fundamental heartbeat frequency and the $2^{nd}$- and even $3^{rd}$-order harmonics caused by the heartbeat motion are separated by the heart rate apart, the heart rate can be recovered when the fundamental heartbeat spectral energy is masked by the much stronger respiratory activity.

Figure 9:
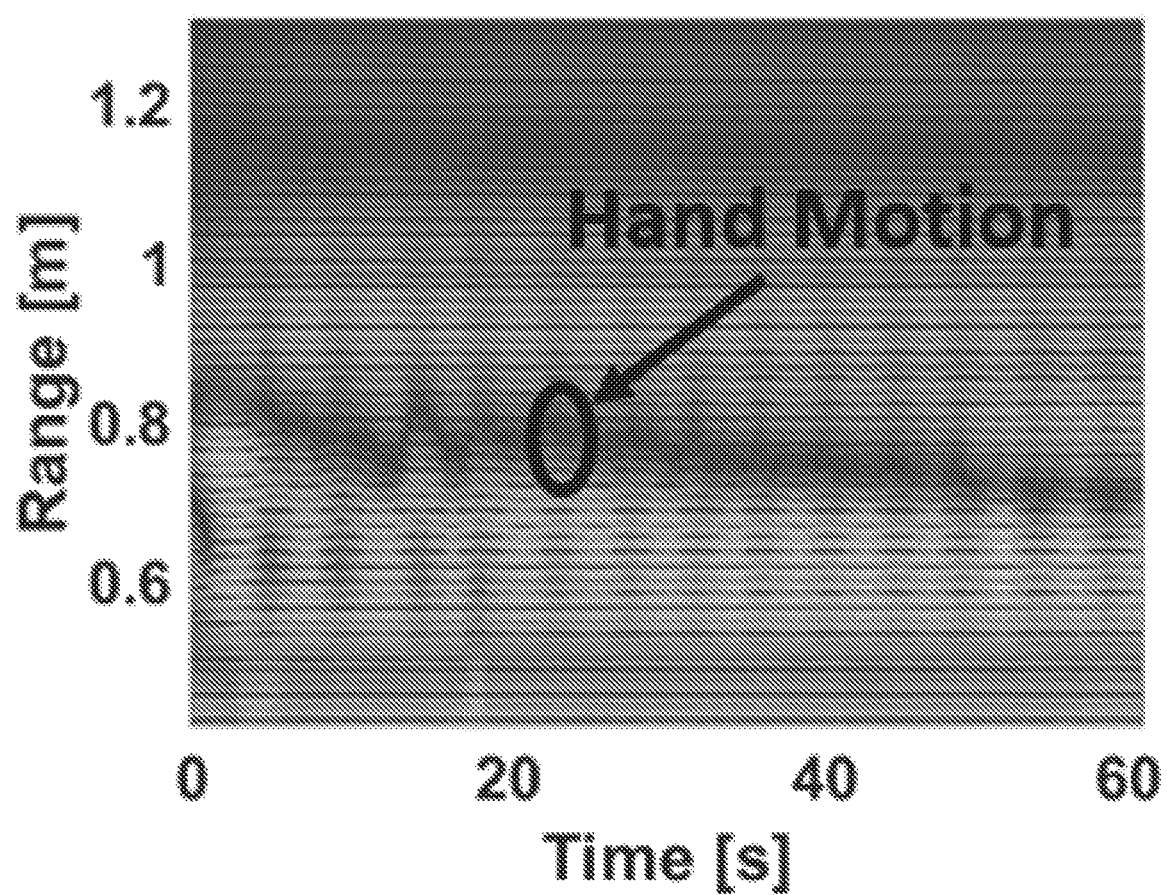
FIG. 9 is a graphical representation of a range-slow-time heatmap during presence of exemplary small-scale motion, illustrating heart-rate monitoring performance.

FIG. 9 is a graphical representation of a range-slow-time heatmap during presence of exemplary small-body motion, such as hand movements. The higher-order harmonics of a heartbeat are robust against such small body motions. In the example of FIG. 9, a test subject is sitting about 0.6 m away from the radar and facing the radar sensor sideway about 45 degrees. During the experiment, the test subject is constantly using a cellphone. The heatmap of FIG. 9 shows that strong energy reflection due to chest motion occurs at about 0.6 m. The motion is spread across quite a few range bins, up to 1 m. In the range direction from 0.67 to 0.85 m, a discontinuity of the energy spread occurs during the entire recording. The respiration pattern fades away at these distances because of the hand motion noise from cellphone usage.

In order to demonstrate that the $2^{nd}$-order harmonic of heartbeat is robust against the hand motion, a range bin is chosen at 0.69 m which contains both the vital signs signal and the hand motion noise. The results are generated in FIGS. 10A-10D.

Figure 10A:
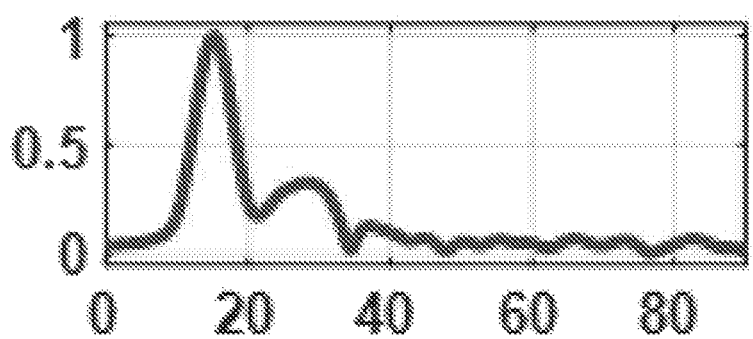
FIG. 10A is a graphical representation of vital signs spectra during the presence of the exemplary small-body motion of FIG. 9 from a complex signal demodulation (CSD) method.
Figure 10B:
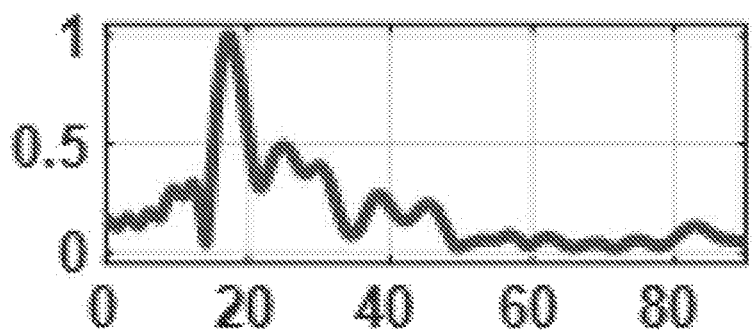
FIG. 10B is a graphical representation of vital signs spectra during the presence of the exemplary small-body motion of FIG. 9 from a phase-based method.
Figure 10C:
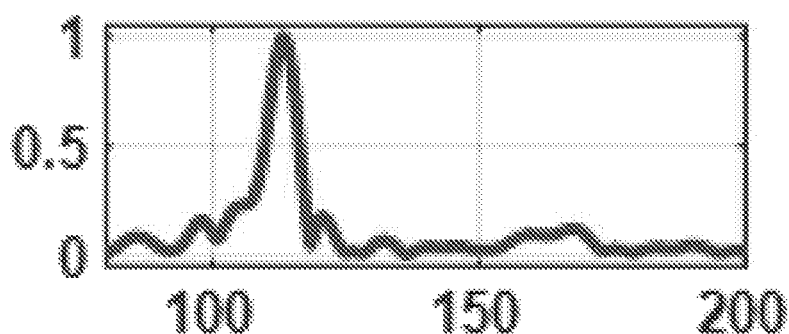
FIG. 10C is a graphical representation of vital signs spectra during the presence of the exemplary small-body motion of FIG. 9 from a $2^{nd}$-order method described herein.
Figure 10D:
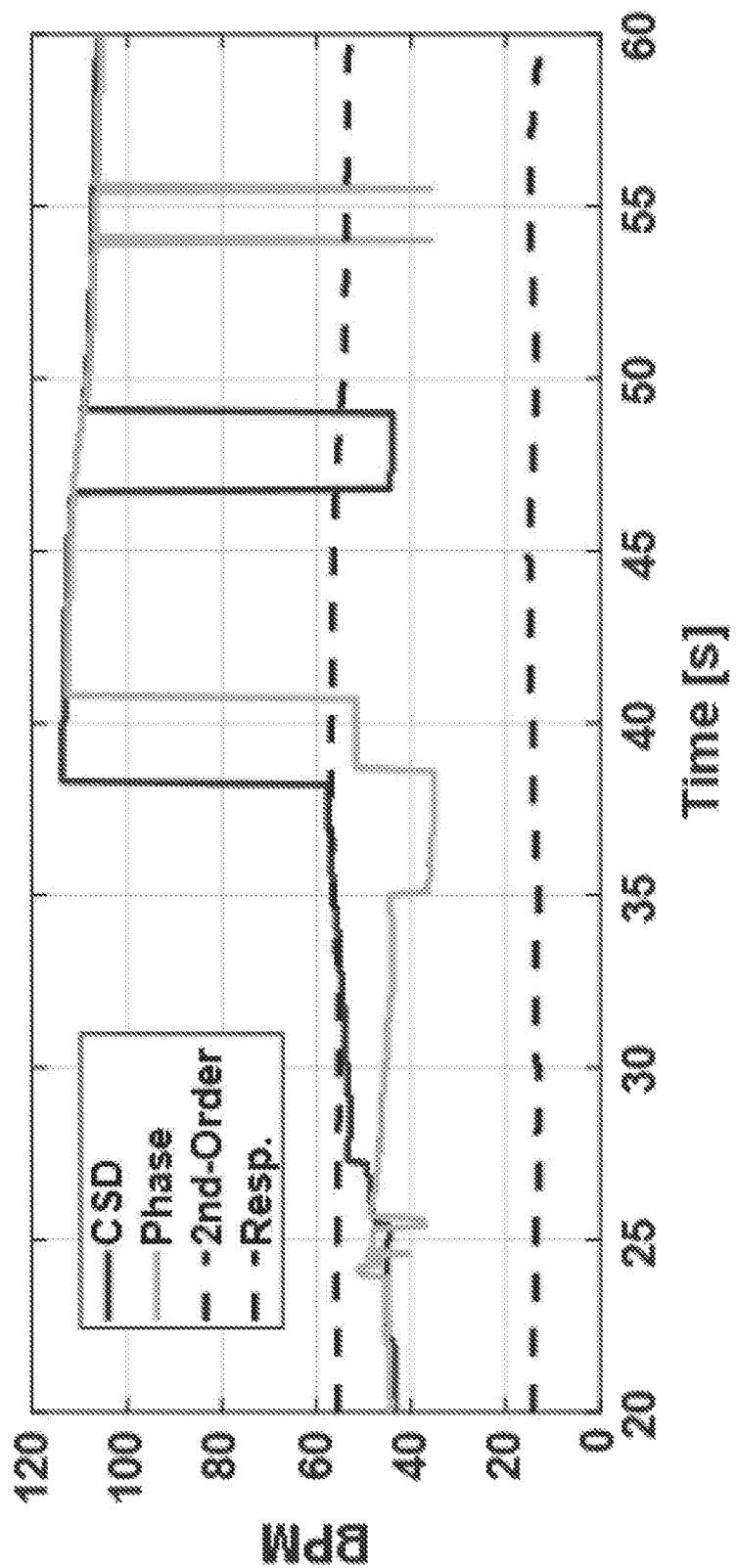
FIG. 10D is a graphical representation of a comparison of continuous measurement results from the different methods of FIGS. 10A-10C.

FIG. 10A is a graphical representation of vital signs spectra during the presence of the exemplary small-body motion of FIG. 9 from a complex signal demodulation (CSD) method. FIG. 10B is a graphical representation of vital signs spectra during the presence of the exemplary small-body motion of FIG. 9 from a phase-based method. FIG. 10C is a graphical representation of vital signs spectra during the presence of the exemplary small-body motion of FIG. 9 from a $2^{nd}$-order method described in this section. Heartbeat information is not present in the lower frequency region due to the constant hand motion noise while in the relatively higher frequency region the trace of the $2^{nd}$-order heartbeat harmonic is clearly visible, and therefore can be readily isolated. FIG. 10D is a graphical representation of a comparison of continuous measurement results from the different methods of FIGS. 10A-10C.

Only the $2^{nd}$-order method can provide consistent and slow-varying estimates over time in the presence of such hand motion. In this manner, locating the higher-order harmonics of heartbeat is robust against small-scale motion artifacts. These heartbeat related higher-order harmonics are noise-limited and almost respiration-free. However, when the test subject is sitting further away from the radar or even behind a wall, the higher-order harmonics can be occasionally below the noise floor. In this situation, an adaptive heart-rate combination method enables continuous heart-rate estimation.

In this adaptive heart-rate combination scheme, two high-pass filters are used to filter out the possible fundamental heartbeat and its higher-order harmonics. For example, two filters can be used with fixed cut-off frequencies, $f_1 = 0.7$ Hz and $f_2 = 1.5$ Hz, roughly corresponding to the normal resting heartbeat 50 BPM to 100 BPM.

The adaptive heart-rate combination works as follows. The algorithm mainly looks for the $2^{nd}$-order and $3^{rd}$-order harmonics of heartbeat by locating the peak location from the spectral content as a result of the harmonics filter. The current heart-rate estimate is computed as one half of the peak location as $f_h^{2nd}/2$. If the current estimate is drifting from the previous estimate by more than 3 beats, the algorithm checks whether the current estimate is from the $3^{rd}$-order harmonic, $f_h^{3rd}/3$. If not, the estimated result from the fundamental heartbeat filter is used instead. In cases that all three estimates are drifting away from the previous estimates, then the algorithm stops and outputs a warning message to the subject (e.g., "Possible movement is observed! Please sit still for next measurement.").

Figure 11:
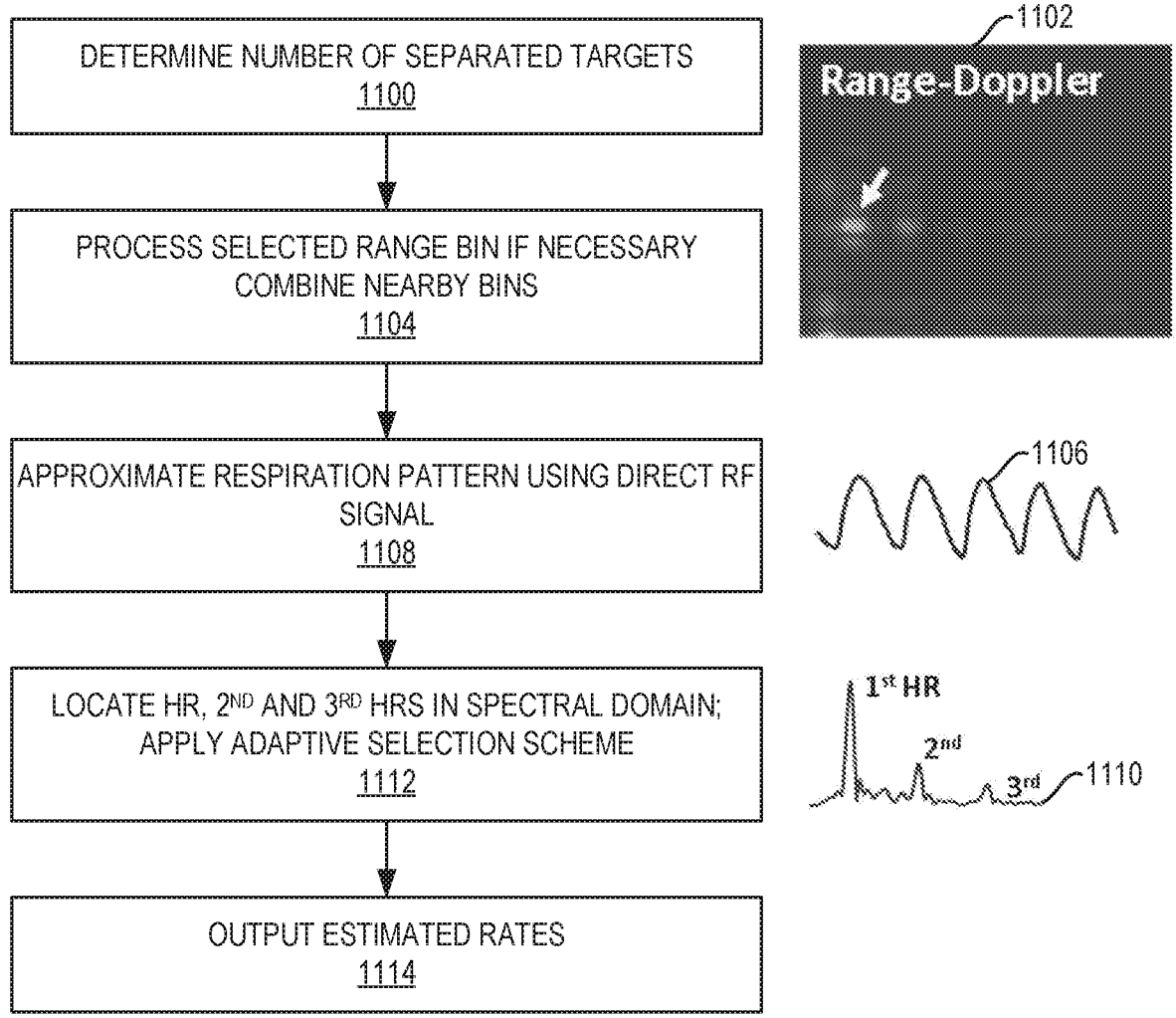
FIG. 11 is a block diagram of a proposed vital signs monitoring algorithm according to embodiments described herein, which may detect vital signs through a wall and/or from multiple subjects.

FIG. 11 is a block diagram of a proposed vital signs monitoring algorithm according to embodiments described herein, which may detect vital signs through a wall and/or from multiple subjects. As an example, it can be assumed that there are two or more subjects positioned apart, with a wall between the subjects and the radar sensor 12. In the processing stage, the received RF signals are recorded. The small micro-motion due to vital signs is extracted by processing the slow-time samples at the range of interest. First, the number of targets in the room is determined (block 1100). This is done by analyzing the range-slow-time heatmap and a range-Doppler map 1102 after removing the static DC component (e.g., background).

Second, once the number of targets has been determined, a range bin can be located for each target (block 1104). The slow-time variation of the RF signal at the selected range bin is a good approximation of the chest motion or respiration pattern 1106 (block 1108).

Third, a spectral analysis is applied at the range bins containing most of the vital signs activity for a given subject (1110). Therefore, the respiration rate is estimated from the location of the dominant spectral peak, and the heart rate is obtained from the proposed adaptive combination scheme described above (block 1112). Estimated vital signals, such as the respiration rate and the heart rate, are then output (block 1114).

Figure 12:
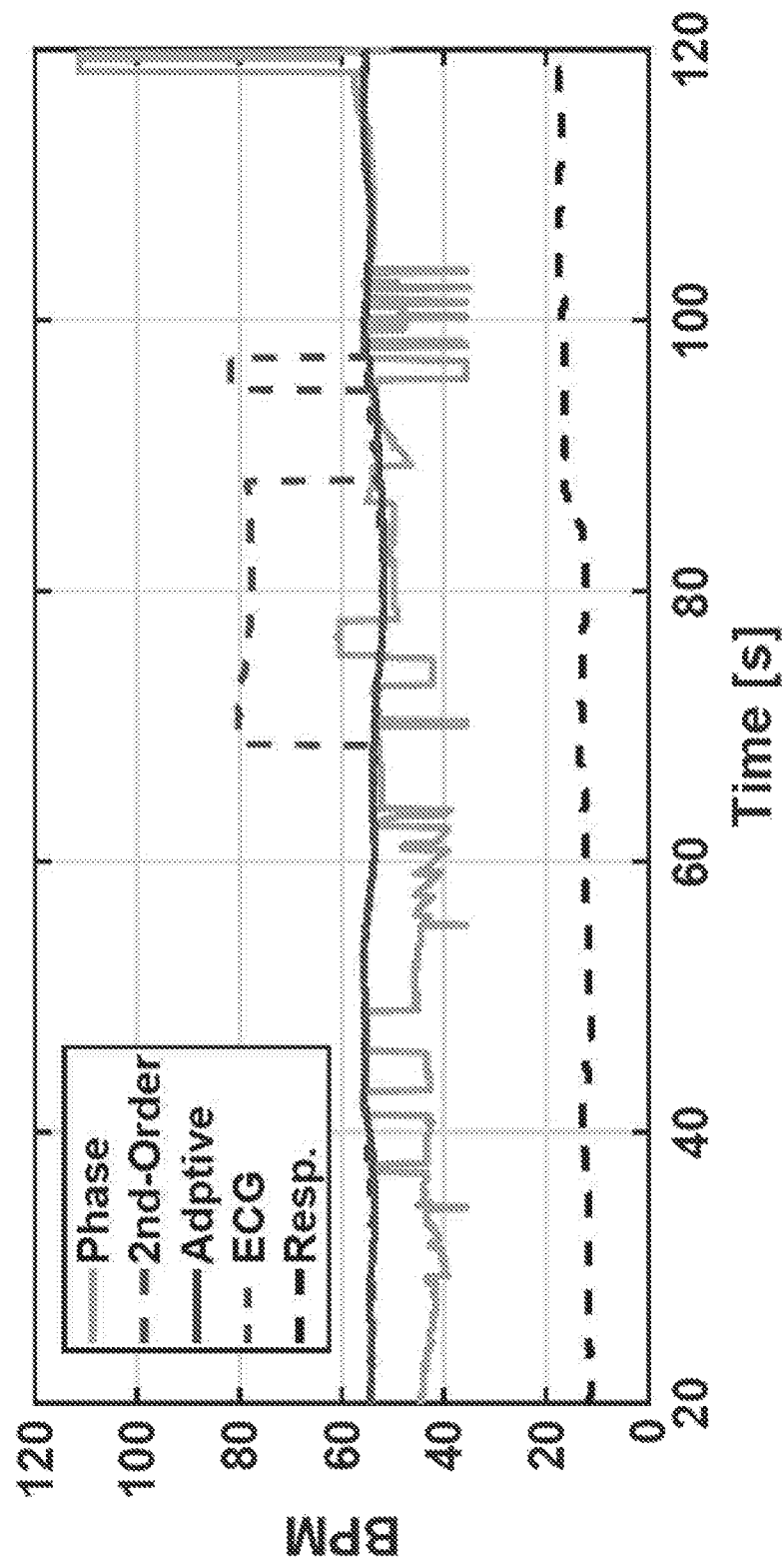
FIG. 12 is a graphical representation comparing performance of the adaptive heart-rate combination with other methods.

FIG. 12 is a graphical representation comparing performance of the adaptive heart-rate combination with other methods. In this example, the continuous measurement results from a test subject about 1 m away breathing normally are demonstrated. Three approaches are compared: a phase-based method, the $2^{nd}$-order method, and the proposed adaptive heart-rate combination method. As shown in FIG. 12, the phase-based method performs poorly due to residual phase noise after phase calibration while the heart-rate estimate from the $2^{nd}$-order harmonic method occasionally drifts away. The overestimates from the $2^{nd}$-order harmonic method come from the stronger $3^{rd}$-order heart-beat harmonic in this representative example. However, the proposed adaptive heart-rate combination method provides accurate estimates throughout the experiment, which is consistent with the reference ECG signal (red dashed curve).

III. BioDrone

Combining radar sensing, such as described above in Section I and Section II, a BioDrone system can deploy radar technology for vital sign monitoring in a flying platform with high agility. One goal of this system is to provide a responsive solution for disaster relief. The BioDrone system provides a fast, safe and flexible way to search for the humans which existing approaches fail to achieve.

Figure 13A:
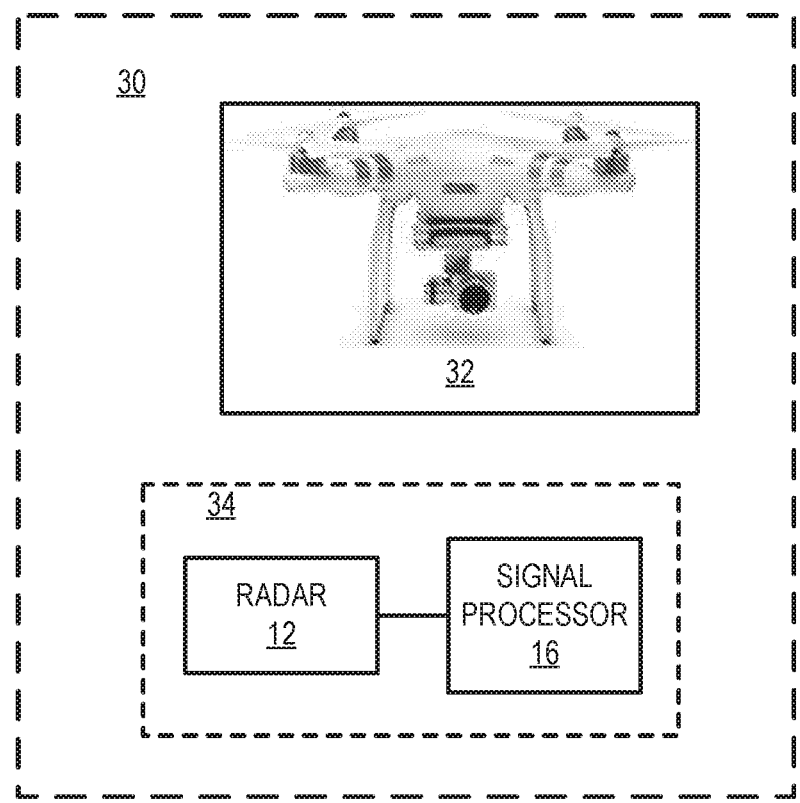
FIG. 13A is a schematic diagram of an exemplary BioDrone system.

FIG. 13A is a schematic diagram of an exemplary BioDrone system 30. The BioDrone system 30 includes an unmanned aerial vehicle (UAV) 32 (e.g., a DJI phantom drone) as the flying platform. The UAV 32 is deployed with a UWB radar sensor 12 and a signal processor 16 (e.g., a stand-alone mini control PC), as well as a portable battery. This forms a sensing module 34 which is used as a payload of the flying platform.

Figure 13B:
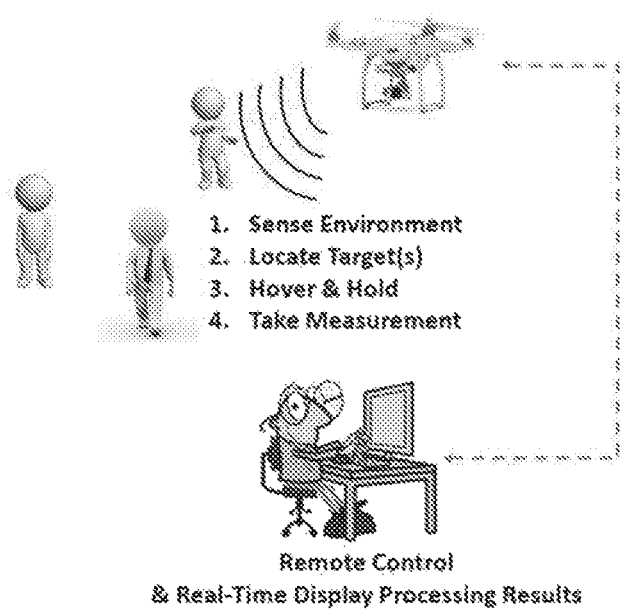
FIG. 13B is a schematic diagram of remote vital sign sensing using the BioDrone system of FIG. 13A.

FIG. 13B is a schematic diagram of remote vital sign sensing using the BioDrone system 30 of FIG. 13A. The proposed system design achieves very promising results. These results show that breathing can be accurately detected when a test subject is under a blanket or behind a wall at distances up to 10 m. A subject's heartbeat can be detected within a few meters.

Figure 14:
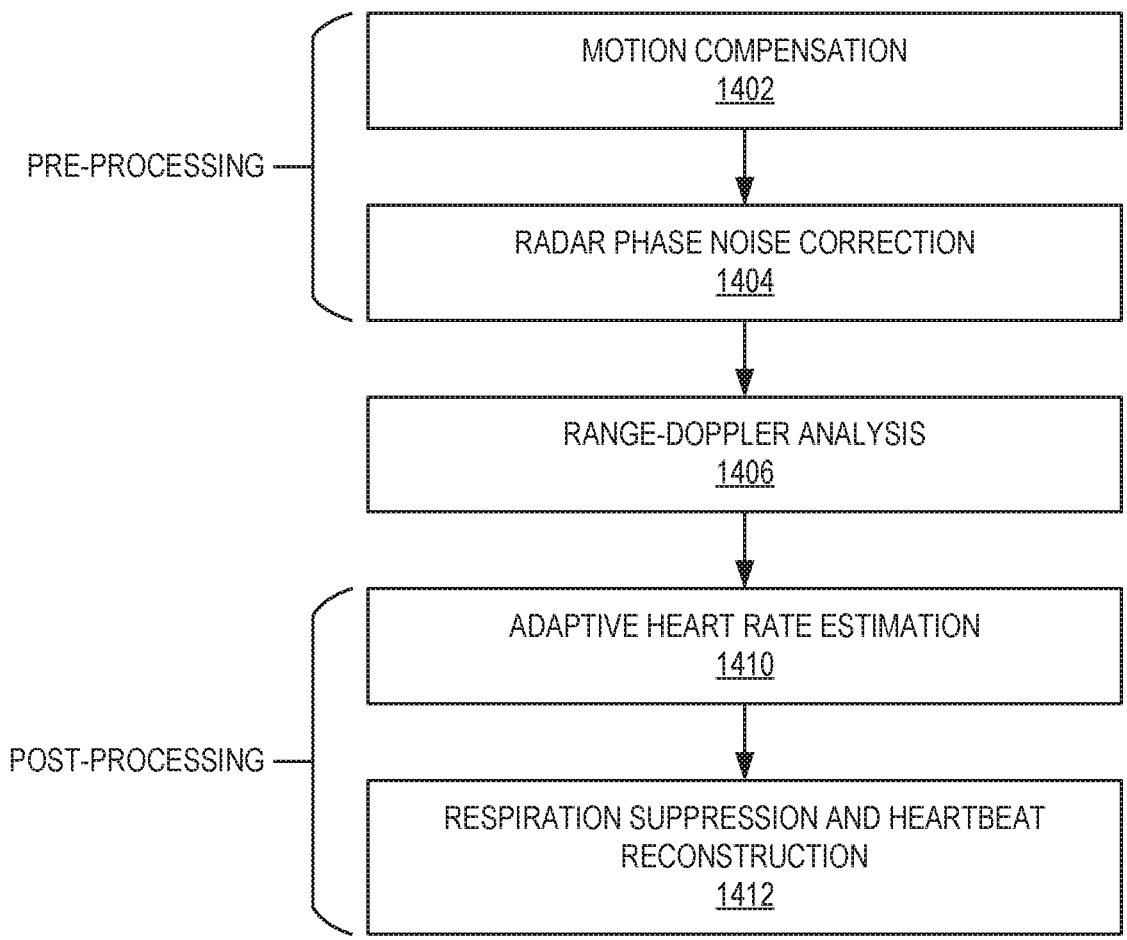
FIG. 14 is a process flow diagram for the BioDrone system of FIG. 13A.

FIG. 14 is a process flow diagram for the BioDrone system 30 of FIG. 13A. An advanced signal processing chain addresses interference from the rotating blades and the constant motion of the flying platform. Even though the measurement only starts when the UAV 32 is at hover and altitude-hold mode, motion jitters are inevitable. These large-scale motion noises are suppressed using a micro-Doppler analysis and a spectral analysis in order to reveal relatively weaker vital sign motions.

In the pre-processing stage, the motion noise from the flying platform and the radar phase noise due to sampling jitters are compensated together since they all lead to increase phase noise level in the received signal (block 1402). Without properly correcting them, the relatively small vital signs motion (especially the heartbeat activity) cannot be detected. In the post-processing stage, spectral domain features related to the heartbeat are used and combined to obtain the rate estimation.

Phase noise reduction in the pre-processing stage is crucial in determination of the heartbeat detectability (block 1404). This is because the platform motion noise even at hover position and the radar sampling jitter can generate a phase noise that can mask the weaker heartbeat signal. The first range sample or zeroth distance sample can be used as a reference to guide the phase noise correction process. A range-doppler analysis (block 1406) is applied at the processing stage. Post-processing includes an adaptive heart rate estimation (block 1410) and respiration suppression and heartbeat reconstruction (block 1412) as described herein.

Figure 15:
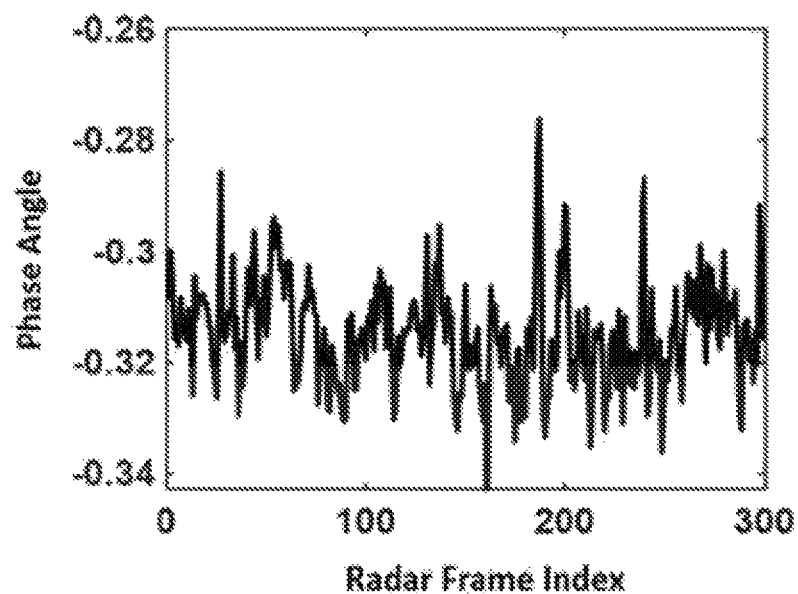
FIG. 15 is a graphical representation of observed phase variation in the BioDrone system of FIG. 13A.

FIG. 15 is a graphical representation of observed phase variation in the BioDrone system 30 of FIG. 13A. Based on this observation, the mean phase center position can be estimated in the first few radar frames (radar scan or radar return). A phase shifter can be applied to the later radar frame by comparing the phase difference between the current phase and the estimated mean phase position.

Figure 16:
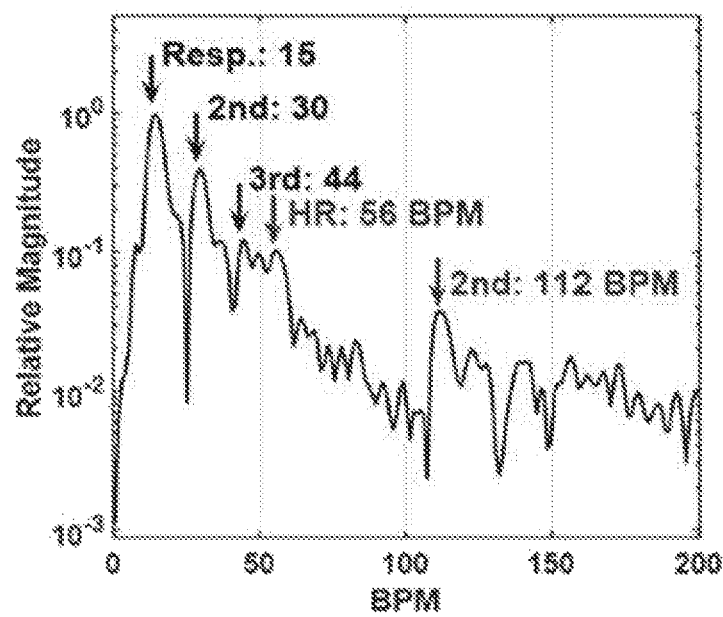
FIG. 16 is a graphical representation of exemplary heartbeat harmonics.

FIG. 16 is a graphical representation of exemplary heartbeat harmonics. When the fundamental heartbeat is masked by the respiration-interference, the heart-rate is recovered using its higher-order spectral features. Therefore, a harmonics based method is first applied to estimate the heart-rate.

Second, a heartbeat waveform reconstruction method is developed motivated by the following facts: 1) due to limited range resolution, the vital signs energies are generally spread across multiple range bins, especially the respiration motion; 2) respiration and heartbeat spectral energies are generally collocated in the range direction while separated in the spectral direction.

Figure 17:
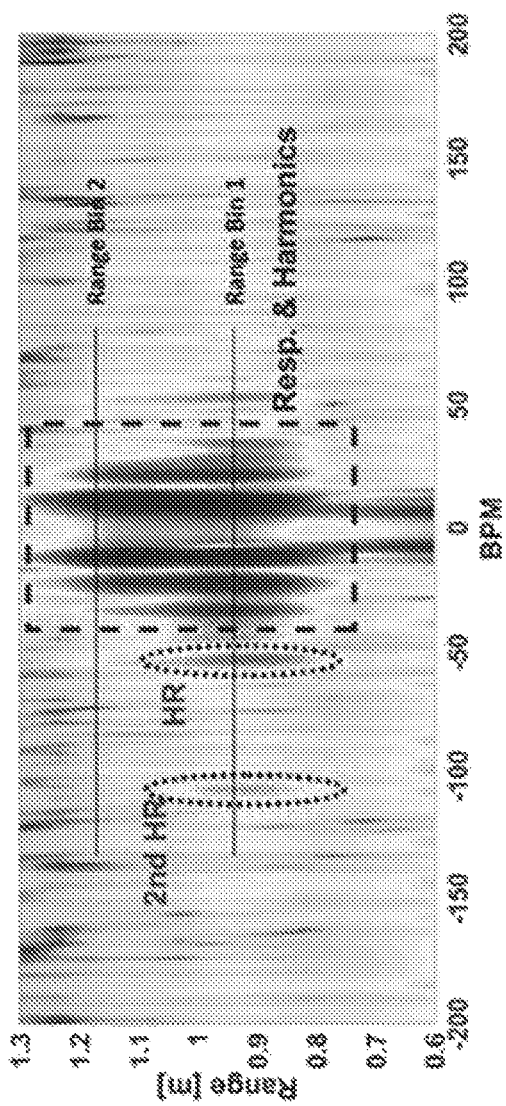
FIG. 17 is a graphical representation of a range-Doppler map for the heartbeat waveform reconstruction method.

FIG. 17 is a graphical representation of a range-Doppler map for the heartbeat waveform reconstruction method. In the waveform reconstruction method, two range bins are selected. One range bin (data in this range bin) is the range bin 1 in FIG. 17, which contains both respiration and heartbeat activities, $s_{Mixed}$. The other range bin is the range bin 2 in FIG. 17, which only contains the respiration activity, $s_{Resp}$. Therefore, the data containing a mixture of vital signs $s_{Mixed}$ can be projected on a null space of the respiration signal.

This projection operator can be estimated using the data containing only the respiration signal $s_{Resp}$. Mathematically, the processing is represented as:

$$P_{Resp}^{\perp} = I - s_{Resp}\{s_{Resp}^{\dagger}s_{Resp}\}s_{Resp}^{\dagger} \qquad \text{Equation 7}$$

$$s_{HR} = P_{Resp}^{\perp} s_{Mixed} \qquad \text{Equation 8}$$

Respiration estimation is a relatively simpler task compared to the heartbeat estimation since it is the dominant motion in the overall vital signs. The rate can be estimated by locating the dominant spectral energy using spectral analysis. The direct radar return at the range bin of interest over time is a good approximation of the respiration pattern.

Figure 18:
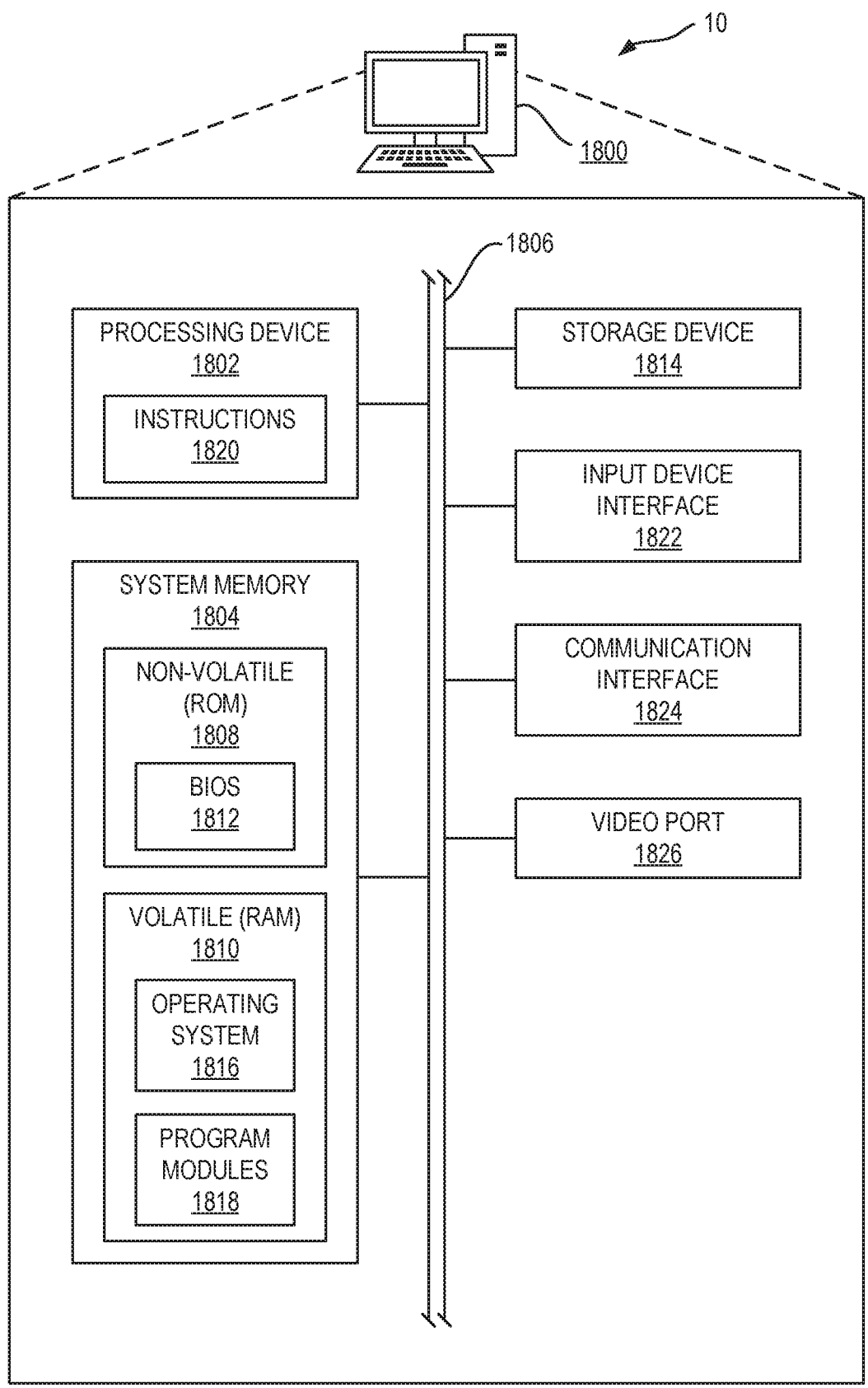
FIG. 18 is a block diagram of the RCG system suitable for implementing cardiac data reconstruction according to embodiments disclosed herein.

FIG. 18 is a block diagram of the RCG system 10 suitable for implementing cardiac data reconstruction according to embodiments disclosed herein. The RCG system 10 includes or is implemented as a computer system 1800, which comprises any computing or electronic device capable of including firmware, hardware, and/or executing software instructions that could be used to perform any of the methods or functions described above. In this regard, the computer system 1800 may be a circuit or circuits included in an electronic board card, such as a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 1800 in this embodiment includes a processing device 1802 or processor, a system memory 1804, and a system bus 1806. The system memory 1804 may include non-volatile memory 1808 and volatile memory 1810. The non-volatile memory 1808 may include read-only memory (ROM), erasable programmable read-only memory (EPROM), electrically erasable programmable read-only memory (EEPROM), and the like. The volatile memory 1810 generally includes random-access memory (RAM) (e.g., dynamic random access memory (DRAM), such as synchronous DRAM (SDRAM)). A basic input/output system (BIOS) 1812 may be stored in the non-volatile memory 1808 and can include the basic routines that help to transfer information between elements within the computer system 1800.

The system bus 1806 provides an interface for system components including, but not limited to, the system memory 1804 and the processing device 1802. The system bus 1806 may be any of several types of bus structures that may further interconnect to a memory bus (with or without a memory controller), a peripheral bus, and/or a local bus using any of a variety of commercially available bus architectures.

The processing device 1802 represents one or more commercially available or proprietary general-purpose processing devices, such as a microprocessor, central processing unit (CPU), or the like. More particularly, the processing device 1802 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1802 is configured to execute processing logic instructions for performing the operations and steps discussed herein.

In this regard, the various illustrative logical blocks, modules, and circuits described in connection with the embodiments disclosed herein may be implemented or performed with the processing device 1802, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 1802 may be a microprocessor, or may be any conventional processor, controller, microcontroller, or state machine. The processing device 1802 may also be implemented as a combination of computing devices (e.g., a combination of a DSP and a microprocessor, a plurality of microprocessors, one or more microprocessors in conjunction with a DSP core, or any other such configuration).

The computer system 1800 may further include or be coupled to a non-transitory computer-readable storage medium, such as a storage device 1814, which may represent an internal or external hard disk drive (HDD), flash memory, or the like. The storage device 1814 and other drives associated with computer-readable media and computer-usable media may provide non-volatile storage of data, data structures, computer-executable instructions, and the like. Although the description of computer-readable media above refers to an HDD, it should be appreciated that other types of media that are readable by a computer, such as optical disks, magnetic cassettes, flash memory cards, cartridges, and the like, may also be used in the operating environment, and, further, that any such media may contain computer-executable instructions for performing novel methods of the disclosed embodiments.

An operating system 1816 and any number of program modules 1818 or other applications can be stored in the volatile memory 1810, wherein the program modules 1818 represent a wide array of computer-executable instructions corresponding to programs, applications, functions, and the like that may implement the functionality described herein in whole or in part, such as through instructions 1820 on the processing device 1802. The program modules 1818 may also reside on the storage mechanism provided by the storage device 1814. As such, all or a portion of the functionality described herein may be implemented as a computer program product stored on a transitory or non-transitory computer-usable or computer-readable storage medium, such as the storage device 1814, non-volatile memory 1808, volatile memory 1810, instructions 1820, and the like. The computer program product includes complex programming instructions, such as complex computer-readable program code, to cause the processing device 1802 to carry out the steps necessary to implement the functions described herein.

An operator, such as the user, may also be able to enter one or more configuration commands to the computer system 1800 through a keyboard, a pointing device such as a mouse, or a touch-sensitive surface, such as the display device, via an input device interface 1822 or remotely through a web interface, terminal program, or the like via a communication interface 1824. The communication interface 1824 may be wired or wireless and facilitate communications with any number of devices via a communications network in a direct or indirect fashion. An output device, such as a display device, can be coupled to the system bus 1806 and driven by a video port 1826. Additional inputs and outputs to the computer system 1800 may be provided through the system bus 1806 as appropriate to implement embodiments described herein.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. An unmanned aerial vehicle (UAV), comprising:
 a radar sensor; and
 a signal processor configured to:
  receive a first radar signal from the radar sensor;
  locate a potential human subject in the first radar signal;
  receive a second radar signal from the radar sensor focused to the potential human subject; and
  extract a vital sign signal of the potential human subject using the second radar signal, wherein extracting the vital sign signal using the second radar signal comprises:
   monitoring first reflections of the second radar signal in radar image pixels, each radar image pixel of the radar image pixels being associated with a different three dimensional (3-D) region in space;
   locating a region of interest based on the first reflections of the second radar signal; and
   continuing to monitor second reflections of a proper subset of the radar image pixels associated with the region of interest to extract a heartbeat waveform from the region of interest.

2. The UAV of claim 1, wherein extracting the vital sign signal comprises:
 determining background noise in the second radar signal; and
 suppressing the background noise.

3. The UAV of claim 1, wherein extracting the vital sign signal comprises:
 estimating motion interference in the second radar signal; and
 suppressing the motion interference to extract the vital sign signal.

4. The UAV of claim 1, wherein the signal processor is further configured to cause the UAV to move toward the potential human subject in response to locating the potential human subject.

5. The UAV of claim 4, wherein extracting the vital sign signal comprises:
 estimating motion interference from the UAV in the second radar signal; and
 suppressing the motion interference to extract the vital sign signal.

* * * * *